US 6,558,314 B1

(12) United States Patent
Adelman et al.

(10) Patent No.: US 6,558,314 B1
(45) Date of Patent: May 6, 2003

(54) DEVICES AND METHOD FOR MANIPULATION OF ORGAN TISSUE

(75) Inventors: Thomas G. Adelman, West Baldwin, ME (US); Frederick J. Foley, Bedford, NH (US); James S. Sharrow, Bloomington, MN (US); Lorraine E. Reeve, Dexter, MI (US); Michael F. Hoey, Shoreview, MN (US)

(73) Assignee: Iotek, Inc., Minneapolis, MN (US)

( * ) Notice: Subject to any disclaimer, the term of this patent is extended or adjusted under 35 U.S.C. 154(b) by 0 days.

(21) Appl. No.: 09/692,524

(22) Filed: Oct. 19, 2000

Related U.S. Application Data

(63) Continuation-in-part of application No. 09/663,917, filed on Sep. 18, 2000.
(60) Provisional application No. 60/210,299, filed on Jun. 8, 2000, and provisional application No. 60/181,925, filed on Feb. 11, 2000.

(51) Int. Cl.[7] .............................. A61F 2/00; A61F 13/00
(52) U.S. Cl. ...................................................... 600/37
(58) Field of Search ........................... 600/37, 16, 201, 600/18, 210, 228, 229, 231, 232, 235; 601/6, 14; 623/3.21; 128/897, 857; 606/191, 1, 201; 5/600

(56) References Cited

U.S. PATENT DOCUMENTS

| | | |
|---|---|---|
| 3,590,815 A | 7/1971 | Schiff |
| 3,608,540 A | 9/1971 | Sartorius |
| 3,613,672 A | 10/1971 | Schiff |
| 3,786,801 A | 1/1974 | Sartorius |
| 3,811,443 A | 5/1974 | Dickinson, III et al. |
| 3,926,192 A | 12/1975 | Van Maren |
| 3,952,737 A | 4/1976 | Lipfert et al. |
| 4,048,990 A | 9/1977 | Goetz |
| 4,543,949 A | 10/1985 | Goepp et al. |
| 4,596,566 A | 6/1986 | Kay |
| 4,635,618 A * | 1/1987 | Munz .............................. 601/6 |
| 4,732,148 A | 3/1988 | L'Esperance, Jr. |
| 4,973,300 A | 11/1990 | Wright |

(List continued on next page.)

FOREIGN PATENT DOCUMENTS

| | | |
|---|---|---|
| EP | 0 157 888 | 10/1985 |
| EP | 0 319 394 | 6/1989 |
| EP | 0 502 485 | 9/1992 |

(List continued on next page.)

OTHER PUBLICATIONS

Borst et al., *Circulation*, 1999, 99:1400–1403.
"Cardiology Device Update," Nov. 15, 1999, Merrill Lynch.
Lowe et al., "Non–Blood–Contacting Riventricular Support: Direct Mechanical Ventricular Actuation," Operative Techniques in Thoracle and Cardiovascular Surgery, vol. 1, No. 1, pp. 345–351, Nov., 1999.

(List continued on next page.)

*Primary Examiner*—Max F. Hindenburg
*Assistant Examiner*—Brian Szmal
(74) *Attorney, Agent, or Firm*—Shumaker & Sieffert, PA

(57) ABSTRACT

Devices and methods of manipulating and stabilizing organ tissue, such as heart tissue. The devices, which are of varying sizes, shapes and conformations, generally include a seal member having a chamber with a wall and a skirt-like member that extends outward from the chamber wall for contact with a surface of an organ. The skirt-like member is substantially compliant and tacky, thereby promoting adhesion with the organ surface. Adherence of the device to the tissue may be enhance by the mechanical or hydraulic application of vacuum pressure. The methods describe steps for manipulating, including moving, lifting, immobilizing, turning and reorienting, organ tissues. Additional methods describe steps for manipulating the heart.

27 Claims, 23 Drawing Sheets

U.S. PATENT DOCUMENTS

| | | |
|---|---|---|
| 4,991,574 A | 2/1991 | Pocknell |
| 5,119,804 A | 6/1992 | Anstadt |
| 5,248,304 A | 9/1993 | Vigdorchik et al. |
| 5,259,836 A | 11/1993 | Thurmond et al. |
| 5,282,785 A | 2/1994 | Shapland et al. |
| 5,423,878 A | 6/1995 | Franz |
| 5,497,771 A | 3/1996 | Rosenheimer |
| 5,499,971 A | 3/1996 | Shapland et al. |
| 5,507,741 A | 4/1996 | L'Esperance, Jr. |
| 5,509,890 A | 4/1996 | Kazama |
| 5,536,243 A | 7/1996 | Jeyendron |
| 5,562,658 A | 10/1996 | Long |
| 5,651,378 A | 7/1997 | Matheny et al. |
| 5,665,105 A | 9/1997 | Furnish et al. |
| 5,727,569 A | 3/1998 | Benetti et al. |
| 5,730,757 A | 3/1998 | Benetti et al. |
| 5,749,892 A | 5/1998 | Vierra et al. |
| 5,762,458 A | 6/1998 | Wang et al. |
| 5,776,154 A | 7/1998 | Taylor et al. |
| 5,779,661 A | 7/1998 | Stephen et al. |
| 5,782,746 A | 7/1998 | Wright |
| 5,799,661 A | 9/1998 | Boyd et al. |
| 5,807,243 A | 9/1998 | Vierra et al. |
| 5,810,721 A | 9/1998 | Mueller et al. |
| 5,836,311 A | 11/1998 | Borst et al. |
| 5,843,019 A | 12/1998 | Eggers et al. |
| 5,855,583 A | 1/1999 | Wang et al. |
| 5,865,730 A | 2/1999 | Fox et al. |
| 5,868,763 A | 2/1999 | Spence et al. |
| 5,871,017 A | 2/1999 | Mayer |
| 5,871,495 A | 2/1999 | Mueller |
| 5,871,496 A | 2/1999 | Ginn et al. |
| 5,875,782 A | 3/1999 | Ferrari et al. |
| 5,885,271 A | 3/1999 | Hamilton et al. |
| 5,888,247 A | 3/1999 | Benetti |
| 5,891,017 A | 4/1999 | Swindle et al. |
| 5,894,843 A | 4/1999 | Benetti et al. |
| 5,899,425 A | 5/1999 | Corey, Jr. et al. |
| 5,906,607 A | 5/1999 | Taylor et al. |
| 5,910,150 A | 6/1999 | Saadat |
| 5,913,876 A | 6/1999 | Taylor et al. |
| 5,921,979 A | 7/1999 | Kovac et al. |
| 5,927,284 A | 7/1999 | Borst et al. |
| 5,931,848 A | 8/1999 | Saadat |
| 5,941,893 A | 8/1999 | Saadat |
| 5,944,730 A | 8/1999 | Nobles et al. |
| 5,944,736 A | 8/1999 | Taylor et al. |
| 5,947,125 A | 9/1999 | Benetti |
| 5,947,896 A | 9/1999 | Sherts et al. |
| 5,957,835 A | 9/1999 | Anderson et al. |
| 5,971,976 A | 10/1999 | Wang et al. |
| 5,972,020 A | 10/1999 | Carpentier et al. |
| 5,976,069 A | 11/1999 | Navia et al. |
| 5,976,123 A | 11/1999 | Baumgardner et al. |
| 5,976,164 A | 11/1999 | Bencini et al. ............. 606/170 |
| 5,984,864 A | 11/1999 | Fox et al. |
| 6,007,486 A | 12/1999 | Hunt et al. |
| 6,007,523 A | 12/1999 | Mangosong |
| 6,013,027 A | 1/2000 | Khan et al. |
| 6,015,378 A | 1/2000 | Borst et al. |
| 6,015,427 A | 1/2000 | Mueller et al. |
| 6,017,304 A | 1/2000 | Vierra et al. |
| 6,019,722 A | 2/2000 | Spence et al. |
| 6,032,672 A | 3/2000 | Taylor |
| 6,036,641 A | 3/2000 | Taylor et al. |
| 6,139,538 A | 10/2000 | Houghton et al. |
| 6,206,827 B1 | 3/2001 | Chin et al. ................... 600/217 |
| 6,231,585 B1 | 5/2001 | Takahashi et al. |
| 6,238,334 B1 * | 5/2001 | Easterbrook et al. ......... 600/16 |
| 6,290,644 B1 | 9/2001 | Green, II et al. |
| 6,306,085 B1 | 10/2001 | Farascioni |
| 6,315,717 B1 | 11/2001 | Benetti et al. |
| 2001/0041827 A1 | 11/2001 | Spence et al. |
| 2002/0002372 A1 | 1/2002 | Jahns et al. |

FOREIGN PATENT DOCUMENTS

| | | | |
|---|---|---|---|
| EP | 0 791 330 A2 | 8/1997 | ........... A61B/17/02 |
| EP | 0 993 806 | 4/2000 | |
| WO | WO 97/26828 | 7/1997 | |
| WO | WO 98/37814 | 9/1998 | |
| WO | WO 99/60929 | 12/1999 | |
| WO | WO 99/60930 | 12/1999 | |
| WO | WO 00/10466 | 3/2000 | |
| WO | WO 00/62680 | 10/2000 | |
| WO | WO 00/74574 | 12/2000 | |
| WO | WO 01/12248 | 2/2001 | |
| WO | WO 01/17437 A3 | 3/2001 | |
| WO | WO 01/17437 A2 | 3/2001 | ........... A61B/17/02 |
| WO | WO 01/80755 | 11/2001 | |

OTHER PUBLICATIONS

Baue et al., "Mechanical Ventricular Assistance in Man," Supplement II to Circulation, vols. XXXVII and XXXVIII, pp. II–33–II36, Apr., 1968.

Nierich et al., "Heart Displacement During Off–Pump CABG: How Well Is It Tolerated?" The Society of Thoracic Surgeons, (Ann Thorac Surg 2000;70:466–72).

"Vacuum Cups and Suction Cups for Eggs and Other Round Objects," 1 page, http://www.anver.com/document/vacuum%20components/vacuum%20cups/cups–egg.htm.

"Vacuum Cup Ball Swivel Spring Suspension Assemblies," 2 pp., http://www.anver.com/document/vacuum%20components/vacuum%20cups/ball_swivel.htm.

"Vacuum Cup Mounting Crossarms, Slides and Suspension Assembly Components," 3 page, http://www.anver.com/document/vacuum%20components/vacuum%20cups/cups–susp–parts.htm.

"Vacuum Cups and Suction Cups Ball Swivel Connectors," 2 pages, http://www.anver.com/document/vacuum%20components/vacuum%20cups/ball_swivel_connectors.htm.

"BST Series 'Soft Touch' Bellows Vacuum Cups," 2 pages, http://www.anver.com/document/vacuum%20components/vacuum%20cups/cups–soft–touch.htm.

"Vacuum Cups with Bonded Metal Inserts," 2 pages, http://www.anver.com/document/vacuum%20components/vacuum%20cups/bonded_inserts.htm.

"Pisco Pneumatic Equipment–Special Fittings," 8 pages, http://www.pisco.com/vacuum.htm.

* cited by examiner

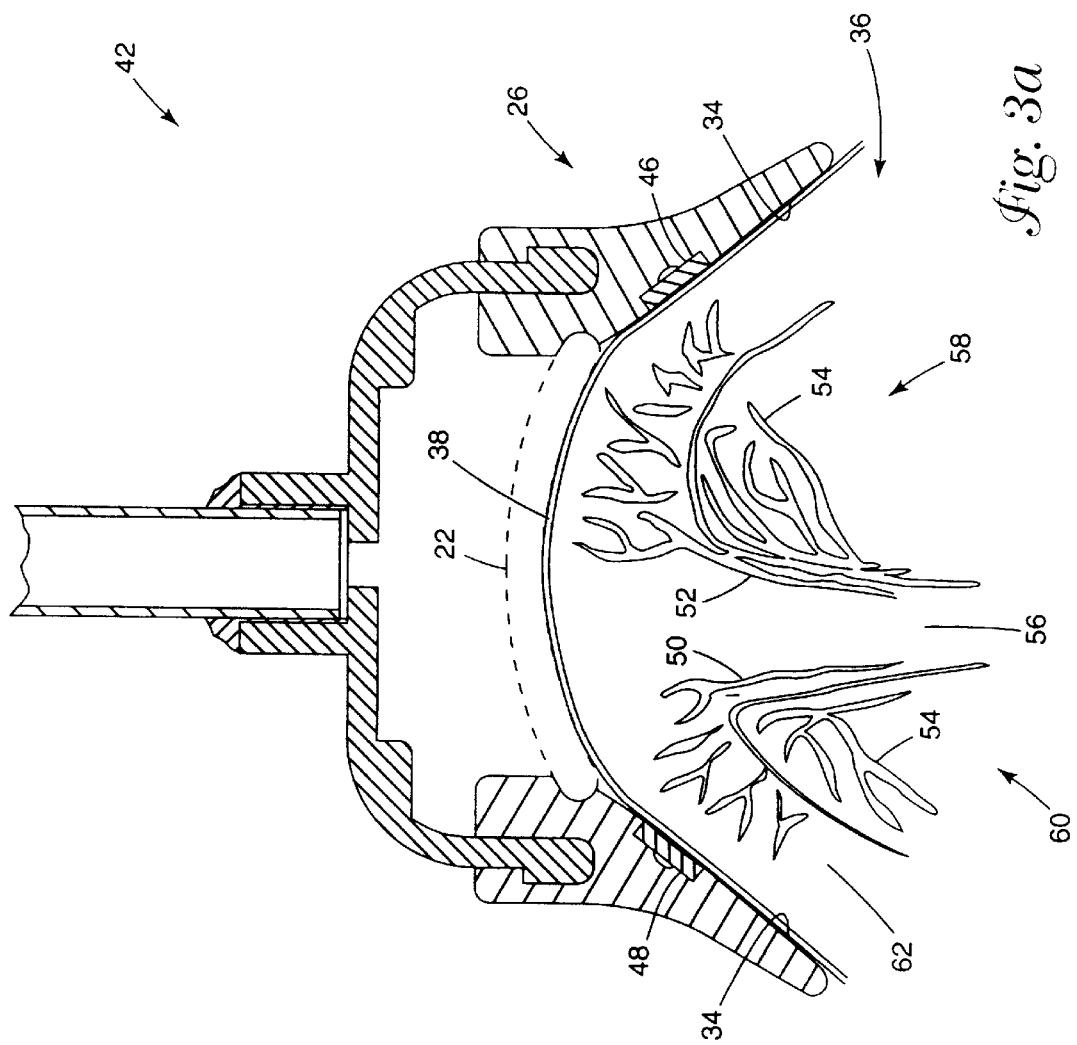

DEVICES AND METHOD FOR MANIPULATION OF ORGAN TISSUE

RELATED APPLICATIONS

This application is a continuation-in-part of U.S. application Ser. No. 09/663,917, filed Sep. 18, 2000, and claims priority from U.S. Provisional Application Serial No. 60/210,299, filed Jun. 8, 2000, and from U.S. Provisional Application Serial No. 60/181,925, filed Feb. 11, 2000, and the entire content of each of which is incorporated herein by reference.

TECHNICAL FIELD

The invention relates to devices capable of providing adherence to organs of the body for purposes of medical diagnosis and treatment. More particularly, the invention relates to devices capable of adhering to, holding, moving, stabilizing or immobilizing an organ.

BACKGROUND

In many areas of surgical practice, it may be desirable to manipulate an internal organ without causing damage to the organ. In some circumstances, the surgeon may wish to turn, lift or otherwise reorient the organ so that surgery may be performed upon it. In other circumstances, the surgeon may simply want to move the organ out of the way. In still other cases, the surgeon may wish to hold the organ, or a portion of it, immobile so that it will not move during the surgical procedure. Unfortunately, many organs are slippery and are difficult to manipulate. Holding an organ with the hands may be undesirable because of the slipperiness of the organ, and because the hands may be bulky, becoming an obstacle to the surgeon. Moreover, the surgeon's hands ordinarily will be necessary for the procedure to be performed. Holding an organ with an instrument may damage the organ, especially if the organ is unduly squeezed, pinched or stretched.

The heart is an organ that may be more effectively treated if it can be manipulated. Many forms of heart manipulation may be useful, including holding the heart, moving it within the chest and immobilizing regions of it. Some forms of heart disease, such as blockages of coronary vessels, may best be treated through procedures performed during open-heart surgery. During open-heart surgery, the patient is typically placed in the supine position. The surgeon performs a median sternotomy, incising and opening the patient's chest. Thereafter, the surgeon may employ a rib-spreader to spread the rib cage apart, and may incise the pericardial sac to obtain access to the heart. For some forms of open-heart surgery, the patient is placed on cardiopulmonary bypass (CPB) and the patient's heart is arrested. Stopping the patient's heart is a frequently chosen procedure, as many coronary procedures are difficult to perform if the heart continues to beat. CPB entails trauma to the patient, with attendant side effects and risks.

Once the surgeon has access to the heart, it may be necessary to lift the heart from the chest or turn it to obtain access to a particular region of interest. Such manipulations are often difficult tasks. The heart is a slippery organ, and it is a challenging task to grip it with a gloved hand or an instrument without causing damage to the heart. Held improperly, the heart may suffer ischemia, hematoma or other trauma. Held insecurely, the heart may drop back into the chest, which may cause trauma to the heart and may interfere with the progress of the operation.

A coronary bypass operation, for example, may involve concerns as to immobilization and as to reorientation of the heart. Once the surgeon has obtained access to the heart, the affected coronary artery may not be accessible without turning or lifting of the heart. Furthermore, the procedure of grafting a new vessel is a delicate one, and contractions of the heart muscle multiply the difficulties in performing the procedure.

Similar concerns may arise in cases where the surgery is far less invasive. In a lateral thoracotomy, for example, the heart may be accessed through a smaller incision in the chest. Arresting of the heart may not be feasible. Yet it may be necessary or desirable for a surgeon to manipulate the heart, such as by moving it or by immobilizing a portion of it during the operation.

SUMMARY

The present invention provides a device for providing adherence to an organ, allowing the organ to be manipulated or immobilized. It should be noted that any references to "adhesion" or related terms do not use the term as it is frequently used in medicine, namely to describe an abnormal union of an organ or part with some other part by formation of fibrous tissue. Rather, "adhesion" and related words refer to adherence, the process of one thing holding fast to another, without them becoming pathologically joined.

There are many circumstances where it may be beneficial to have the present invention provide adherence to an organ. A surgeon may have a need, for example, simply to lift a gall bladder out of the way to access another organ. A more complex environment in which the present invention may be used is that of open-heart surgery. In this context, a surgeon may employ several forms of the present invention during a single operation, depending upon the need and the application. By selecting the form of the present invention that suits the task at hand, the surgeon may reduce the risk of trauma to the patient and improve the effectiveness of the surgery. Because the device may have multiple uses within open heart surgery, application of the device to heart tissue will be described in detail herein, with the understanding that the device may have application to other areas of medical practice as well.

The device may include a seal member that allows it to adhere to slippery bodily tissue, such as the surface of a heart. The surgeon may lift the heart or reposition it by manipulating the device, with the seal member adhering to the surface of the heart. The device may also be applied to the heart in a form in which the coronary contractions near the site of adhesion are minimized, effectively stabilizing or immobilizing an area of the heart. Adherence of the device is temporary, not permanent. The device can be configured to apply easily to the tissue, adhere firmly, remain adhered as long as needed, minimize the risk of accidental release, and release easily when needed. Importantly, the device can be designed to minimize the risk of tissue trauma that may result from adherence and release.

Upon engagement of the seal member with the surface of the heart, the seal member defines a chamber. The seal member may further define a vacuum port in fluid communication with the chamber. The seal member can be made, in part, of a compliant material that will permit it to conform to the surface of the heart and that will further permit it to maintain contact while the heart is contracting. In some cases, adherence may be improved by application of the vacuum pressure from a pump by way of the vacuum port, where at least a portion of the seal member deforms and substantially forms a seal against the surface. In other cases, adherence may be improved by other mechanical or hydraulic devices.

In some embodiments, the seal member may define multiple cavities and multiple vacuum ports, each vacuum port in fluid communication with each cavity. Upon application of independent vacuum pressure to each vacuum port, at least a portion of the seal member deforms and substantially forms a seal against the surface, providing vacuum-assisted adhesion between the device and the heart. Employment of multiple chambers and multiple vacuum ports, with independent vacuum pressure applied to each port, can provide an additional measure of safety. Leakage in one of the sealed chambers will not affect the others, and adhesion may be maintained even if the seal on one chamber fails.

The adherence of the device can be aided by the use of particular materials to form the seal member. In particular, the chamber may be defined in part by a semi-rigid material, e.g., formed in a cup-like shape, that provides the device with structural integrity, and prevents the seal member from collapsing under vacuum pressure. The seal member also may include a skirt-like member, however, that is coupled to the chamber. The skirt-like member can be formed from a tacky, deformable material that promotes adhesion to the heart tissue at the point of contact. In some embodiments, the tacky, deformable material may take the form of a silicone gel that is molded, cast, deposited, or otherwise formed to produce the skirt-like member. With such a material, it may be possible to fix the seal member to the heart tissue even when no vacuum pressure is applied by a pump.

When a tacky, deformable material is used in combination with vacuum pressure, the device may adhere to the heart safely and securely, and may permit the surgeon to reorient the heart or to immobilize a region of it. The semi-rigid chamber portion imparts structural integrity to the seal member, while the tacky, deformable material forming the skirt-like member provides a seal interface with the heart tissue that is both adherent and adaptive to the contour of the heart. Moreover, as the skirt-like member deforms, it produces an increased surface area for contact with the heart tissue. The increased surface area provides a greater overall contact area for adherence, and distributes the coupling force of the vacuum pressure over a larger tissue area to reduce tissue trauma.

In general, materials suitable for forming the chamber may be too rigid, and may cause ischemia, hematoma or other trauma to the heart. The incorporation of a deformable, skirt-like member, in accordance with the present invention, provides a buffer between the more rigid chamber material and the heart tissue. Materials of the kind ordinarily used to form the chamber also provide little if any tackiness. By contrast, tacky materials ordinarily are not well suited for adherence in conjunction with a vacuum. A device in accordance with the present invention provides a two-part construction that exploits the advantages of both types of materials. In particular, the less deformable material forms a chamber that stands up to vacuum pressure, while the more deformable, tacky material forms a skirt-like member that provides an atraumatic yet robust seal interface with the heart tissue.

In one embodiment, the present invention provides an organ manipulation device comprising a seal member having a chamber with a wall and a skirt-like member that extends outward from the chamber wall for contact with a surface of an organ. The skirt-like member is substantially compliant and tacky, thereby promoting adhesion with the organ surface. The device may include a vacuum port in fluid communication with an interior of the chamber, and may further include a valve that regulates fluid flow through the vacuum port. The device may be of a variety of shapes and sizes.

In another embodiment, the present invention provides a method for manipulating a heart, the method comprising engaging a seal member with the apex of the heart to define a chamber, at least a portion of the seal member being compliant and adhesive to heart tissue, applying vacuum pressure to a vacuum port associated with the chamber such that a portion of the seal member deforms to substantially seal the chamber against leakage, and using the seal member as a gripping point for lifting and turning the heart. The method may further include pacing the heart by applying electrical voltage or current to the apex of the heart through electrodes incorporated within the seal member.

The present invention also provides an alternative method for manipulating a heart, the method comprising engaging a seal member with the apex of the heart to define a chamber, at least a portion of the seal member being compliant and adhesive to heart tissue, and the seal member including an aperture and a flexible airtight and watertight membrane, drawing the membrane toward the aperture such that a portion of the seal member deforms to substantially seal the chamber against leakage, and using the seal member as a gripping point for lifting and turning the heart. The membrane may be drawn mechanically or hydraulically.

In a further embodiment, the invention provides a method for immobilizing a region of the heart, the method comprising using a seal member to define a region of immobilization, engaging a seal member with the surface of the heart to define a cavity, at least a portion of the seal member being compliant and adhesive to heart tissue, and applying vacuum pressure to a vacuum port associated with the cavity such that a portion of the seal member deforms to substantially seal the cavity against leakage.

The details of one or more embodiments of the present invention are set forth in the accompanying drawings and the description below. Other features, objects, and advantages of the present invention will be apparent from the description and drawings, and from the claims.

BRIEF DESCRIPTION OF THE DRAWINGS

FIG. 3a presents a cross-sectional side view of another embodiment of the present invention, being used to engage the apex of the heart.

Like reference numerals are used throughout the drawings to indicate like elements.

DETAILED DESCRIPTION

Figure 1:
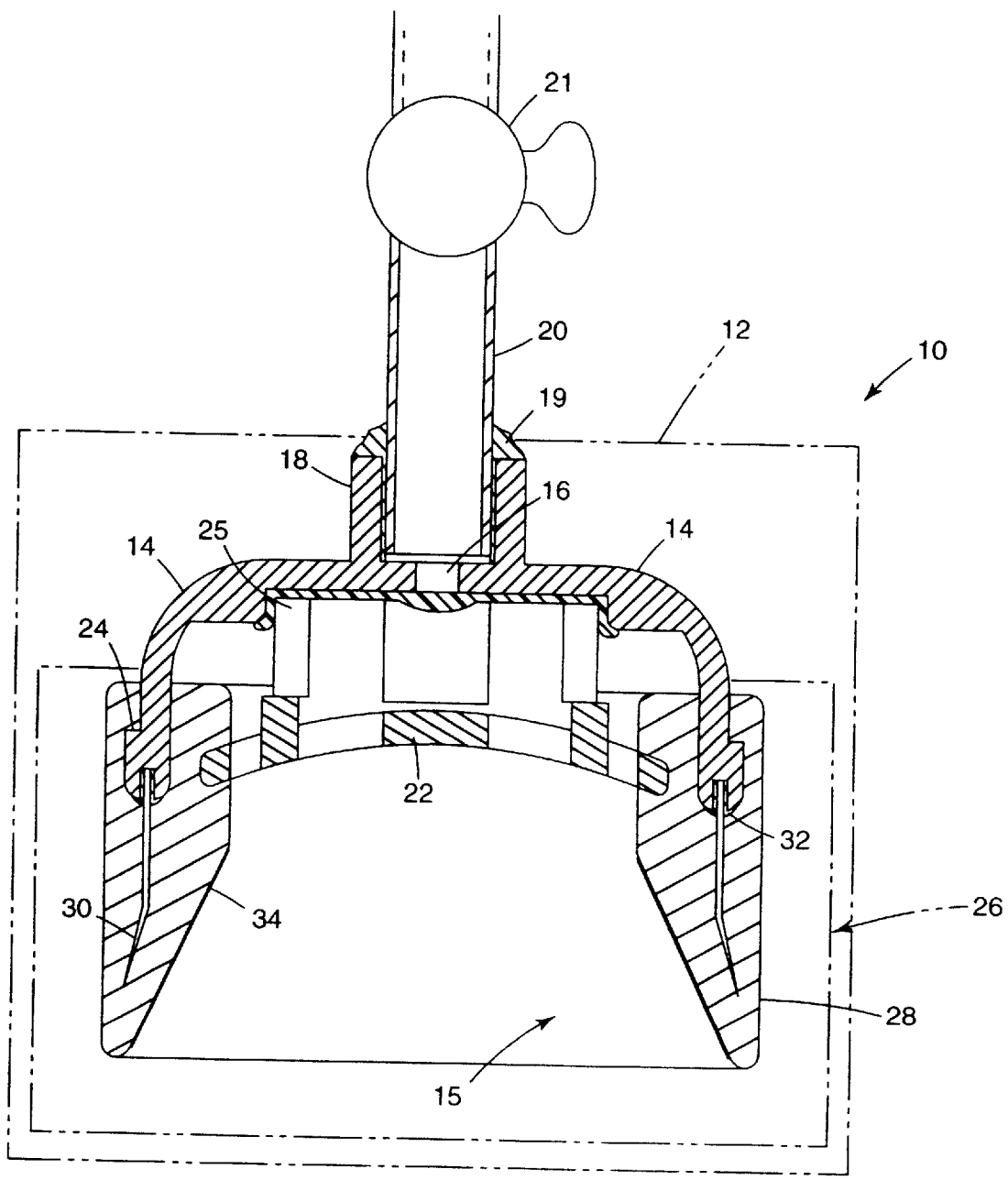
FIG. 1 presents a cross-sectional side view of one embodiment of the present invention.

FIG. 1 is a cross-sectional view of a device 10 for organ manipulation, in accordance with an embodiment of the present invention. As shown in FIG. 1, device 10 may include a seal member 12. Seal member 12 may include cup-like member 14. Cup-like member 14 defines a general size and shape of the device 10, and may include components to serve various purposes. In the example of FIG. 1, cup-like member 14 defines a generally circular structure suitable for forming a cup-like shape. Cup-like member 14 may include a vacuum port 16 and a neck 18 suitable for receiving a vacuum tube 20. Vacuum tube 20 may be sealed in neck 18 with sealant 19. Vacuum tube 20 may include a valve such as stopcock 21, to prevent air from moving through vacuum tube 20, or to allow a quick release of vacuum pressure. Alternatively, a valve may be included in vacuum port 16 or neck 18.

The cup-like member 14 may encompass a spacer 22 to prevent the tissue from being drawn too far into the chamber, and especially from being drawn into vacuum port 16, when vacuum pressure is applied. Although spacer 22 may be integrally formed with member 14, spacer 22 is shown in FIG. 1 as a separate element. Spacer 22 may bear against an inner ring 25. Spacer 22 may also be omitted from device 10. Cup-like member 14 may also include a flange 24 that aids the physical connection between cup-like member 14 and a skirt-like member 26. The interior wall of cup-like member 14 and skirt-like member 26 define a chamber 15. In addition to providing a basic structural framework of device 10, cup-like member 14 provides a firm structure by which device 10 may be securely gripped by a surgeon or by an instrument. Cup-like member 14 may include a structure such as a handle, knob or other attachment (not shown) for this purpose.

As shown in FIG. 1, device 10 is not adhering to any tissue, and chamber 15 is open rather than enclosed. Upon engagement of seal member 12 with the surface of the tissue, chamber 15 becomes enclosed. Vacuum port 16 may be in fluid communication with chamber 15. Seal member 12 can be made, in part, of a compliant material that will permit it to conform to the surface of the organ. In the case of engagement between seal member 12 and a heart, the compliant qualities of seal member 12 will permit seal member 12 to maintain contact while the heart is contracting and relaxing.

In some cases, adherence to the tissue may be improved by application of the vacuum pressure by way of vacuum port 16 and vacuum tube 20, where at least a portion of seal member 12 deforms and substantially forms a seal against the surface of the tissue. Vacuum pressure may be supplied by a number of devices, such as by a syringe, and may be maintained by shutting stopcock 21. A constant source of negative pressure may be employed but is not necessary.

Cup-like member 14 may be formed from many materials, including thermoplastic such as polycarbonate, ABS, polysulfone, polyester and polyurethane, and including corrosion-resistant metals such as titanium, and including rigid and semi-rigid elastomers such as silicone rubber, natural rubber, synthetic rubber, and polyurethane. Cup-like member 14 may have a semi-rigid structure that may be somewhat compliant, but generally resistant to deformation. Skirt-like member 26, in contrast, may be formed from a substantially compliant material, such as a silicone gel, hydrogel or closed cell foam. Skirt-like member 26 generally permits deformation upon contact with tissue. In this manner, cup-like member 14 imparts structural integrity to device 10, while skirt-like member 26 provides a seal interface with the tissue. Also, the material forming skirt-like member 26 may be tacky, and thereby promote adhesion to the surface of the tissue.

The adhesive effectiveness of skirt-like member 26 may be aided not only by the tackiness of the material, but the greater surface area provided at the seal interface upon deformation. Skirt-like member 26 surrounds and may be coupled to flange 24 of cup-like member. In the embodiment shown in FIG. 1, the skirt-like member includes three components. One component is main ring 28, which is made of a compliant material that can deform, but will ordinarily not deform sufficiently as to rupture any seal. Main ring 28 forms the general perimeter of the chamber 15. A second component is a reinforcing element 30, partly embedded within the main ring 28 and anchored by a fixing mechanism 32 within flange 24 of cup-like member.

One embodiment of reinforcing element 30 is a spring or wire or shape-memory metal that generally resists deformation, and resultant collapse of main ring 28 under vacuum pressure. Reinforcing element 30 will allow main ring 28 to deform, but not to deform sufficiently as to rupture the seal during use. Employment of reinforcing element 30 may make it possible to make main ring 28 of skirt-like member 26 from less material. A third component of the skirt-like member 26 is a layer of tacky material 34 on a region around main ring 28 where the seal will be formed. Tacky material 34 can adhere to organ tissue and can easily release in the absence of an applied vacuum. Tacky material 34 can also be compliant, permitting it to conform to the tissue in contact with it. Tacky material 34 can be coated or molded on main ring 28, or bonded to main ring 28 as a discrete component. It is also possible that main ring 28 may be made entirely of tacky material 34.

A material suitable for the main ring 28 and the tacky material 34 is a biocompatible silicone gel. Examples of suitable silicone gels are MED-6340 and GEL-8 150, both commercially available from NuSil Silicone Technologies of Carpinteria, Calif. Each gel is provided as a two-component liquid, the components designated Part A and Part B, which may be blended together. The properties of the silicone depend generally upon the ratio of the mixture of Part A and Part B. In general, increasing the ratio of Part A to Part B produces a softer and tackier gel, while increasing the ratio of Part B to Part A produces a firmer and less tacky gel. Like silicone elastomers, silicone gels can be manufactured with a range of crosslink densities. Silicone gels, however, generally do not contain reinforcing filler and therefore have a much higher degree of malleability and conformability to desired surfaces. As a result, the compliance and tackiness of silicone gel materials can be exploited in skirt-like member 26 to provide a more effective seal. For skirt-like member 26, the MED 6340 silicone gel material, for example, exhibits a hardness characteristic such that a 19.5 gram shaft with a 6.35 mm diameter has been observed to penetrate the gel approximately 5 mm in approximately 5 seconds. This hardness characteristic is not a requirement, but merely representative of that exhibited by the commercially available MED 6340 material.

One mixture blends MED-8150 Part A and Part B in approximately a proportion of 3 units of Part A to 7 units of Part B, i.e., in approximately a 3:7 ratio. When mixed in an A:B ratio of approximately 3:7, the resulting silicone gel is suitable for use as main ring 28. This mixing ratio produces a material of little tackiness but of sufficient firmness that it will not disconnect from cup-like member. Even though the gel is firm, however, it is also soft and deformable, and in the shape of a cup may be pressed against organ tissue without causing serious trauma. A skirt-like member 26 made entirely from the firmer gel would be expected to provide a good vacuum seal, but little tackiness and resultant adherence would be provided. A mixture blending MED-6340 in approximately a ratio of 4.5:5.5 produces a comparable material suitable for use as main ring 28.

When MED-6340 is mixed in an A:B ratio of approximately 1:1, according to a preferred embodiment, the resulting silicone gel is suitable for use as the tacky material 34. The 1:1 mixing ratio produces a material of considerable tackiness. The material adheres well to slippery organs such as the heart, and is also easily moldable. In addition, the material minimizes tissue abrasion. The material is significantly softer than the silicone gel used to form the main ring 28. The softer gel poses virtually no risk of trauma to the heart. A skirt-like member 26 made entirely from the softer gel would be expected, however, to deform easily in the presence of a vacuum and quickly to rupture the vacuum seal. Skirt-like member 26 can be formed, for example, by insert-molding of main ring 28 and tacky material 34. Skirt-like member 26 then can be adhesively bonded or otherwise coupled to cup-like member 14. Alternatively, cup-like member 14 also can be insert-molded with one or both of main ring 28 and tacky material 34 to produce the integrated seal member 12. The combination of the softer gel forming tacky material 34, the firmer gel forming the main ring 28, and reinforcement from the reinforcing member 30 produces a skirt-like member 26 that adheres to the surface of the heart, can conform to the surface of the heart when vacuum pressure is applied, yet will not deform to an extent to rupture the vacuum seal. This combination is able to absorb the shock of the beating heart without rupturing the seal and without damaging the cardiac tissue. The softness and greater surface area contact provided by the tacky material 34 upon deformation reduces the possibility of tissue trauma.

Figure 2:
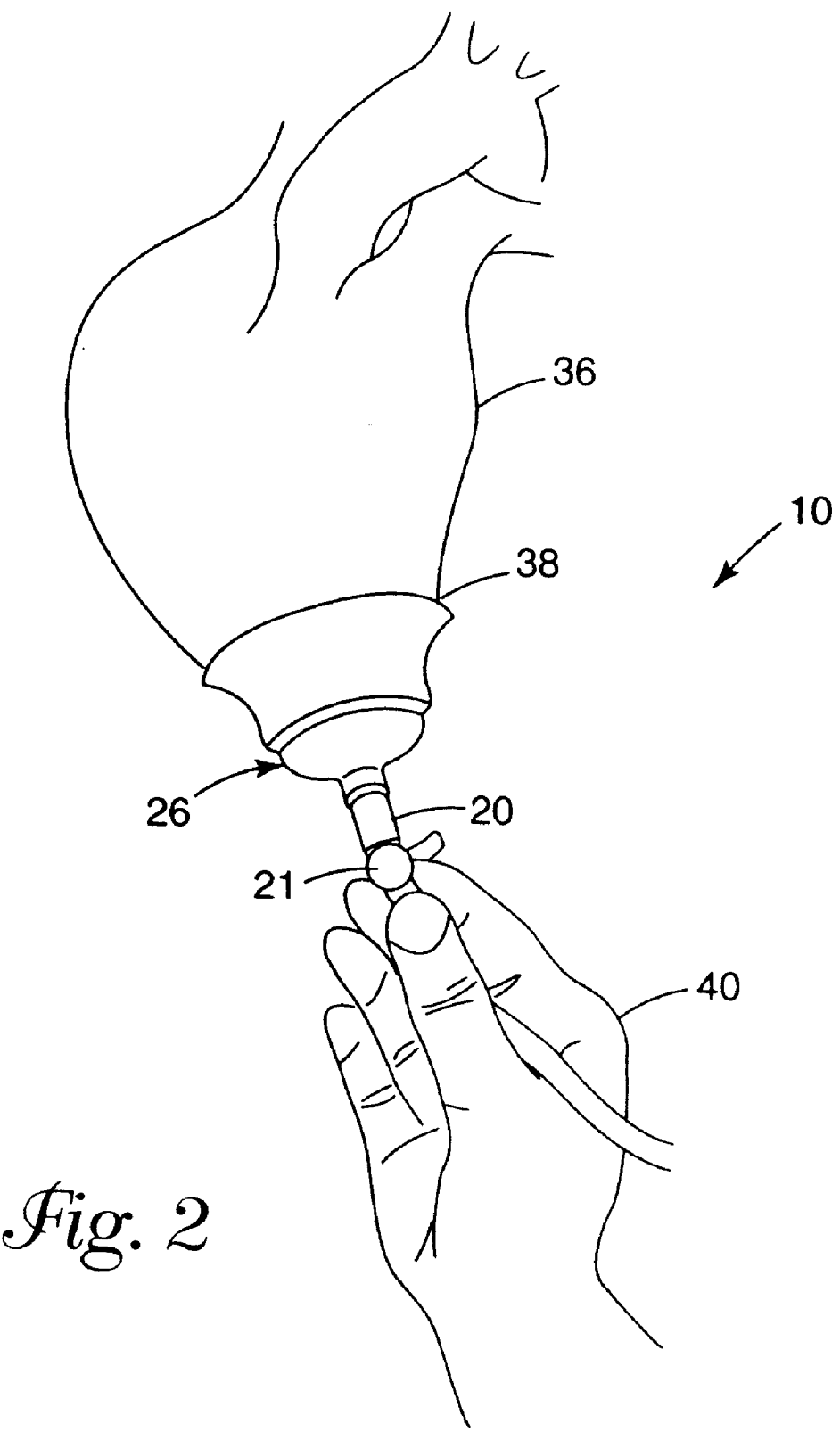
FIG. 2 presents a perspective view of the embodiment of the invention depicted in FIG. 1, being used to manipulate the heart.

FIG. 2 shows device 10 of FIG. 1 in an exemplary application. A surgeon 40 has obtained access to a heart 36 and has placed the device 10 over the apex 38 of the heart 36. The heart 36 has not been arrested. Device 10 has adhered to apex 38. If valve 21 on device 10 is left in the open position, the beating motion of the heart and the pressure of the surgeon's hand 40 will allow the heart tissue to move into the interior of chamber 15, displacing air from the chamber. The beating of the heart 36 naturally causes the apex 38 to rotate or twist reversibly to a degree during each contraction. The rotational movement causes the apex 38 to move into seal member 12, thereby expelling air through vacuum tube 20 and open valve 21, and engaging deformable skirt-like member 26. The surgeon 40 can determine visually and tactilely whether the apex 38 has penetrated the skirt-like member 26 or come in contact with the spacer 22. When the apex 38 has penetrated the skirt-like member 26, the valve 21 is closed, preventing air from entering the device 10 and creating a partial vacuum or negative pressure in the device. Atmospheric pressure acts to keep device 10 affixed to the heart tissue. No external vacuum source is required to create the partial vacuum. Moreover, the partial vacuum or negative pressure is sufficient to permit lifting of the apex 38 as shown in FIG. 2, and can support moving the heart 36 through a ninety-degree arc. The material employed to form skirt-like member 26 is sufficiently flexible and compressible that skirt-like member 26 conforms tightly to the shape of heart 36, yet the material is also atraumatic to the myocardial tissue. The apex 38 continues to twist during each contraction, but the seal member 12 holds the apex without causing trauma. Removal of device 10 can be accomplished by opening valve 21, and allowing air to move through vacuum tube 20 to separate heart tissue from the inner surface of skirt-like member 26. If necessary, a syringe or other means can be used to force air through tube 20 to facilitate rapid detachment of device 10 from heart 36. Alternatively, an external vacuum source can be applied via vacuum tube 20 to remove air from inside device 10 and permit atmospheric pressure to hold the device to the tissue at apex 38. Valve 21 can be closed to prevent air from entering tube 20, and the external vacuum source can be removed. No additional external vacuum source is then required. Tacky material 34 shown in FIG. 1 helps promote adhesion. Compliant skirt-like member 26 of the device has conformed to the shape of apex 38 to create an airtight seal around the heart tissue. The compliance of skirt-like member 26 allows the seal to be maintained even as the heart 36 contracts. Stopcock 21 has been closed, so that a vacuum seal between device 10 and apex 38 may be maintained without constant application of vacuum pressure. With the combination of vacuum pressure and tackiness, surgeon 40 may move the heart 36 by manipulating the device 10 or the vacuum tube 20. FIG. 2 shows the surgeon 40 beginning to lift the apex 38 by holding the vacuum tube 20. By lifting the apex 38, the surgeon 40 may move the heart 36 about and obtain access to other areas of the heart. The beating heart 36 may be manipulated in this way so as not to compromise the heart's hemodynamic functions. In particular, the surgeon 40 may lift the heart 36 with device 10 without causing a drop in aortic blood pressure. In addition, device 10 provides a robust seal with the heart 36, allowing manipulation of the heart 36 without the need for other supporting devices, and is also atraumatic to the apex 38, avoiding ischemia, hematoma or other trauma.

The overall size of the device 10 relative to the heart may vary. In open-heart surgery, for example, a larger cup-like device may be most useful. In less invasive procedures, a smaller cup-like device, sized for insertion though an incision or through a cannula, may be more useful.

FIG. 3a shows a cutaway view of a device 42 for organ manipulation, in accordance with an embodiment of the present invention. Device 42 is similar to device 10 of FIG. 1 in overall shape and construction, and device 42 is shown in an exemplary application similar to FIG. 2. In particular, device 42 has been placed over the apex 38 of the heart 36. The heart 36 has not been arrested. Device 42 has adhered to apex 38. Adherence may be promoted by tacky material 34 and by the application of vacuum pressure.

Figure 3B:
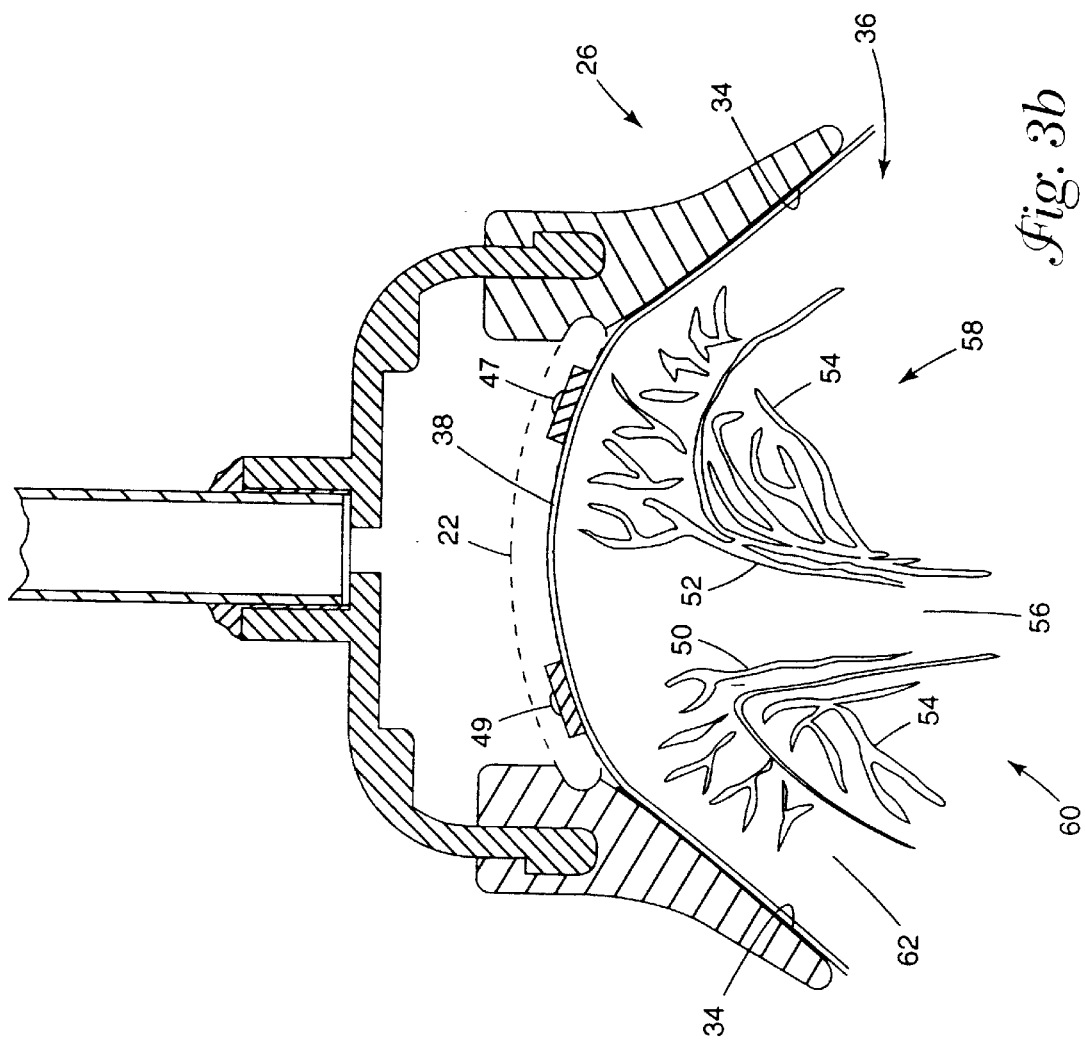
FIG. 3b presents a cross-sectional side view of another embodiment of the present invention, being used to engage the apex of the heart.

Device 42 includes electrodes 46, 48, which may be used to pace the heart 36 by stimulation of the bundles of His 50, 52 and Purkinje fibers 54. Alternately, electrodes 47 and 49 can be positioned on spacer 22, as shown in FIG. 3b, or at other locations within the device. The normal pacemaker of the heart is the sinoatrial (SA) node (not shown in FIG. 3a). The SA node is a small specialized region in the right atrial wall near the opening of the superior vena cava. An action potential initiated within the SA node ordinarily spreads to both atria of the heart. An internodal pathway extends from the SA node to the atrioventricular (AV) node (not shown in FIG. 3a), which is a small bundle of specialized cardiac muscle cells near the junction of the atria and the ventricles 58, 60. Specialized cells known as the bundle of His extend from the AV node, through the ventricular septum 56, where they divide into the left branch bundle of His 50 and the right branch bundle of His 52. The branch bundles of His 50, 52 curve around the tip of the ventricular chambers 60, 58 and travel back toward the atria along the outer walls of the heart 36. Following receipt of an impulse by the AV node from the SA node, and after a brief AV nodal delay, the impulse travels rapidly down the bundles of His 50, 52. Purkinje fibers 54 extend from the bundles of His 50, 52 and spread throughout the ventricular myocardium 62. The impulse transmitted by the bundles of His 50, 52 is carried throughout the ventricular myocardium 62 by Purkinje fibers 54. The bundles of His 50, 52 and Purkinje fibers 54 have a normal rate of action potential discharge of 20 to 40 action potentials per minute. Stimulation of the bundles of His 50, 52 and Purkinje fibers 54 may cause the ventricular myocardium to beat at a faster rate and thus to help pace the heart 36. Electrodes 46, 48, 47 and 49, which may be coupled to a voltage or current source (not shown in FIG. 3a or 3b) via conductors, may in this way be used to stimulate the bundles of His 50, 52 and Purkinje fibers 54 and help pace the heart 36. Because skirt-like member 28 adheres atraumatically to the apex 38, the device 42 can remain on the apex 38 for long periods of time without causing hematoma or other trauma. In addition, the placement of device 42 on the apex 38 allows for minimal interference with the surgical field. Consequently, device 42 can pace the heart 36 when needed, and can remain in place when pacing is not required.

Figure 4:
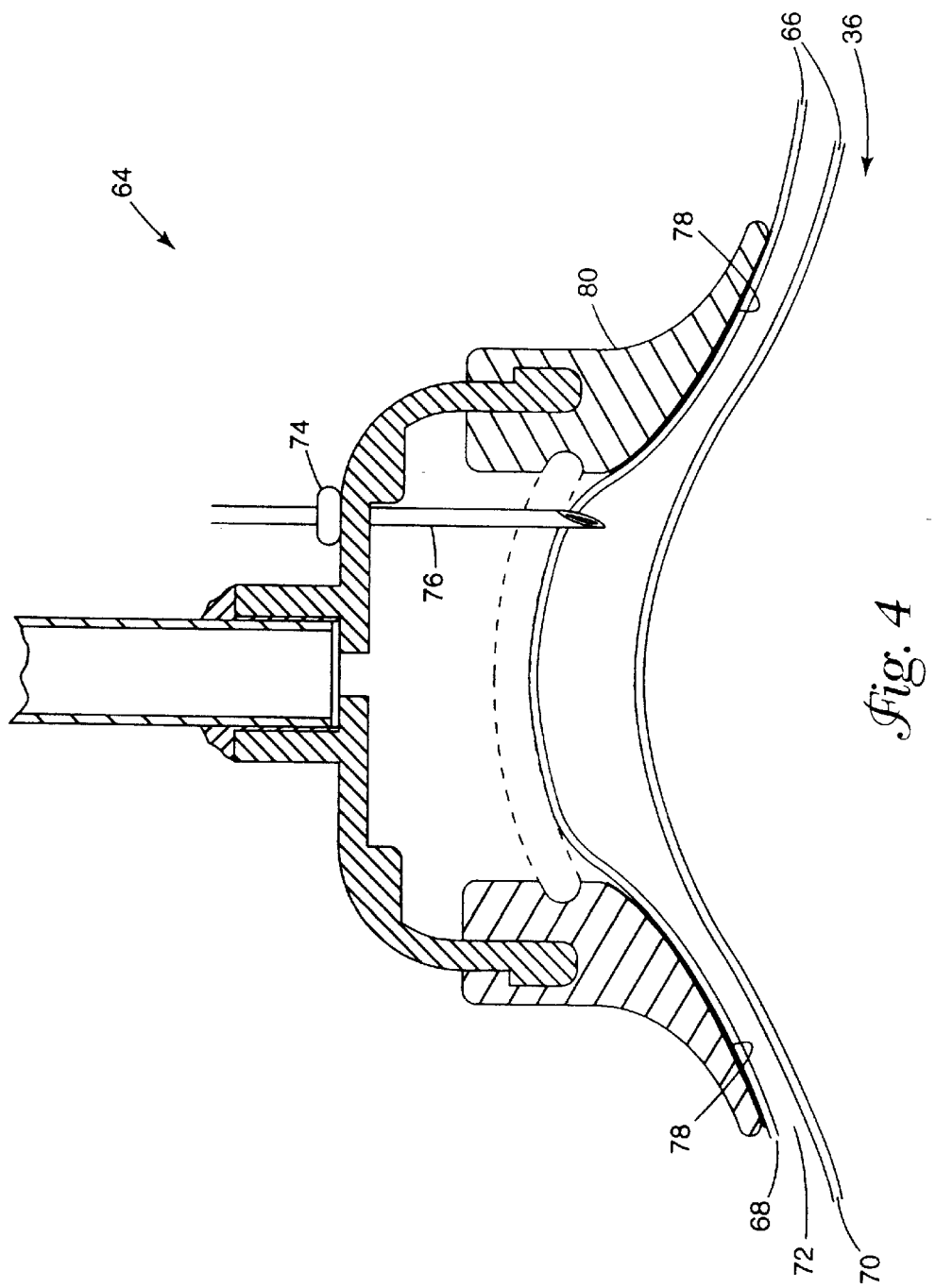
FIG. 4 presents a cross-sectional side view of another embodiment of the present invention, being used to administer medicinal agents to the lumen of the pericardial sac.

FIG. 4 shows a cutaway view of device 64 for organ manipulation, in accordance with an embodiment of the present invention. Device 64 is similar to device 10 of FIG. 1. Device 64 is shown in another exemplary application. In the surgical operation depicted in FIG. 4, the pericardial sac 66 surrounding the heart has not been opened. The pericardial sac 66 is a double-walled membranous sac that encloses the heart 36. The sac 66 is a tough, fibrous membrane known as the pericardium 68. The surface of the heart is known as the epicardium 70. Pericardial fluid in the sac 72 lubricates the epicardial layer 70 and reduces friction between the pericardial and epicardial layers as the heart 36 beats. The device shown in FIG. 4 allows for medicinal agents to be introduced into the pericardial sac 66. Device 64 shown in FIG. 4 is like the device 10 shown in FIG. 1, except that device 64 includes a port 74 to allow for drug delivery. A needle 76 has been introduced through the port 74. Device 64 had been placed upon the pericardial sac 66 and adheres due to the tackiness of the tacky material 78 lining the skirt-like member 80. Vacuum pressure has been applied to draw the outer layer of the pericardium 68 toward the needle 76. This procedure will generally not draw the epicardium 70 as much. By drawing the pericardium 68 toward needle 76, needle 76 may penetrate only the pericardium 68 and not the epicardium 70, and medicinal agents may be effectively delivered to the pericardial fluid 72 of the pericardial sac 66. Delivery of medicinal agents in this manner may be useful, for example, when injecting epinephrine, or when treating a viral or bacterial infection affecting the pericardial sac 66 known as pericarditis.

Figure 5:
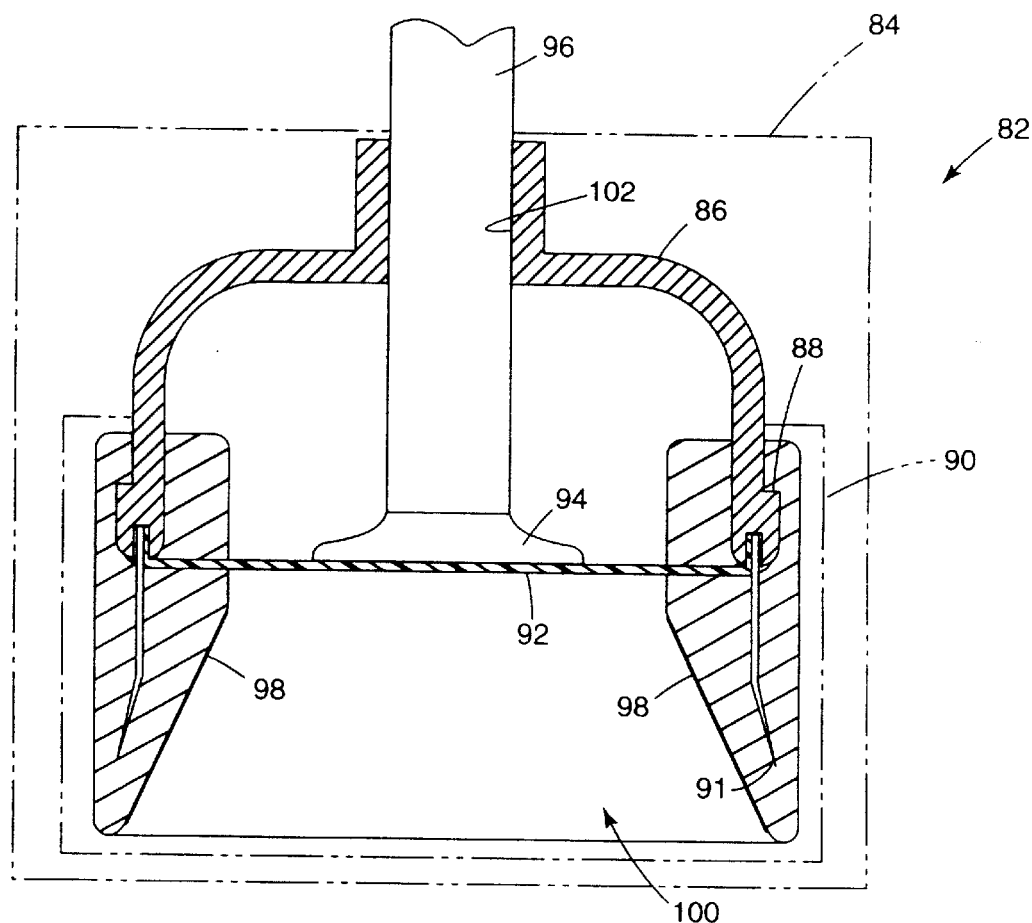
FIG. 5 presents a cross-sectional side view of another embodiment of the present invention.

FIG. 5 is a cross-sectional view of another device 82 for organ manipulation, in accordance with an embodiment of the present invention. Device 82 may include a seal member 84. Seal member 84 may include a cup-like member 86. Cup-like member 86 defines a general size and shape of the device 82, and as shown in FIG. 5 defines a generally circular structure suitable for forming a cup-like shape. Cup-like member 86 may also include a flange 88 that aids the physical connection between member 86 and a skirt-like member 90. Skirt-like member 90 is similar to skirt-like member 26 in FIG. 1. Skirt-like member 90 optionally can include a reinforcing element 91.

Seal member 84 may engage the surface of organ tissue. Seal member 84 can be made, in part, of a compliant material that will permit it to conform to the surface of the organ. Skirt-like member 90 may include tacky material 98 that can conform to and easily adhere to organ tissue. In addition, device 82 may include a membrane 92 affixed at an interface between cup-like member 86 and skirt-like member 90. Membrane 92 and skirt-like member 90 define a chamber 100. Membrane 92 may be constructed of a flexible airtight and watertight material that may be stretched without rupturing. Materials that may be suitable for use as membrane 92 may include elastomers such as silicone rubber. Elasticity of membrane 92 may vary, but membrane of approximately 30 durometer may be sufficiently elastic. A disk 94 made of substantially semi-rigid or hard elastomer material may be affixed to the center of membrane 92. Preferably membrane 92 is affixed to disk 94 at every point of contact between membrane 92 and disk 94. A shaft 96 made of substantially rigid material may be affixed to the center of disk 94. Disk 94 would preferably be nonuniform in thickness, i.e., narrowed or thinned at the extremities. Cup-like member 86 may include an aperture 102 through which shaft 96 may extend.

Figure 6:
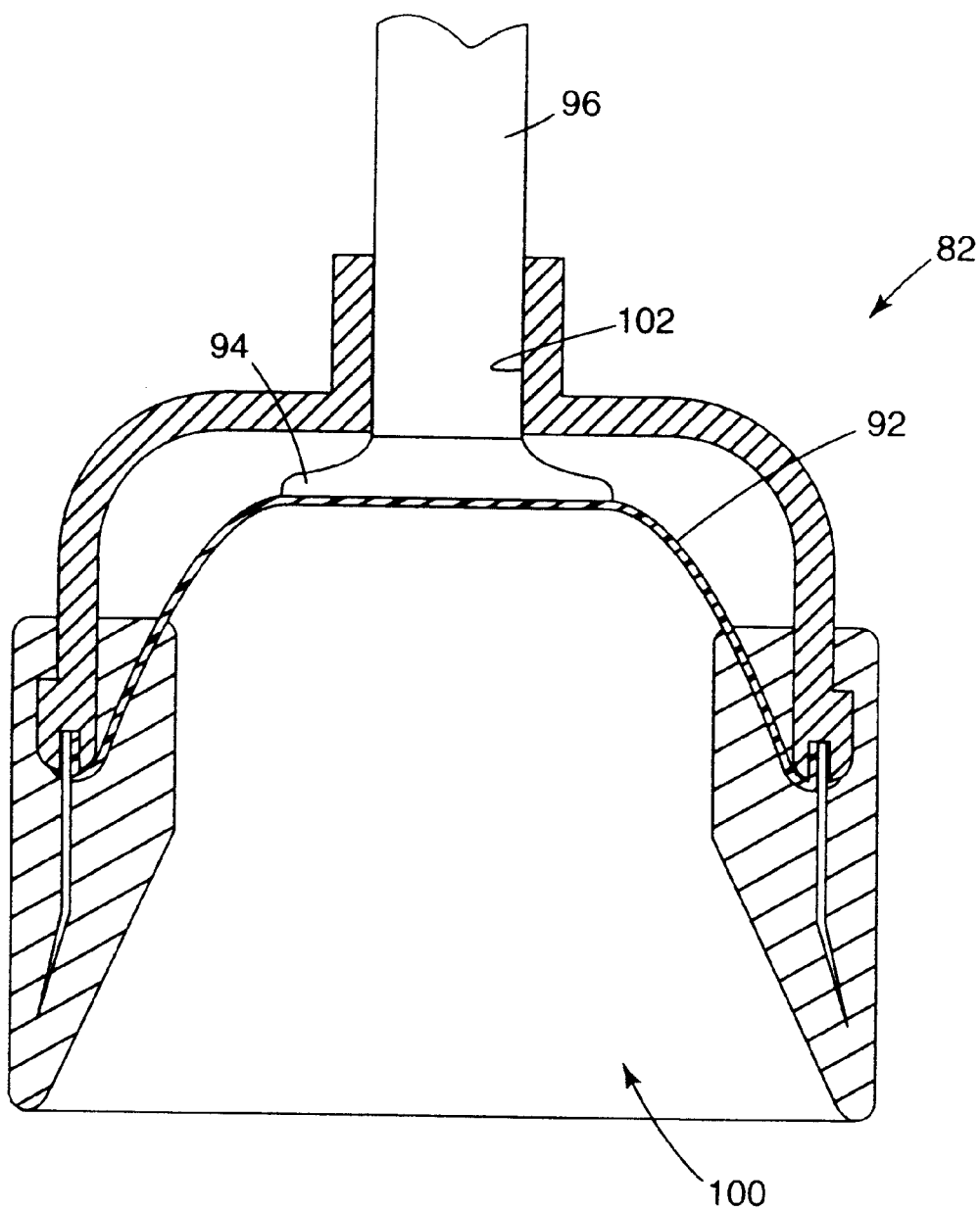
FIG. 6 presents a cross-sectional side view of the embodiment of the invention depicted in FIG. 5, with shaft partially withdrawn.

FIG. 6 is a cross-sectional view of device 82. FIG. 6 is like FIG. 5, except shaft 96 is shown partly extracted. By keeping cup-like member 86 stationary and extracting shaft 96, membrane 92 is pulled toward aperture 102, and chamber 100 is thereby enlarged. A stopping mechanism (not shown) such as a thumbscrew or a clamp may be employed to maintain the position of shaft 96 relative to member 86.

Figure 7:
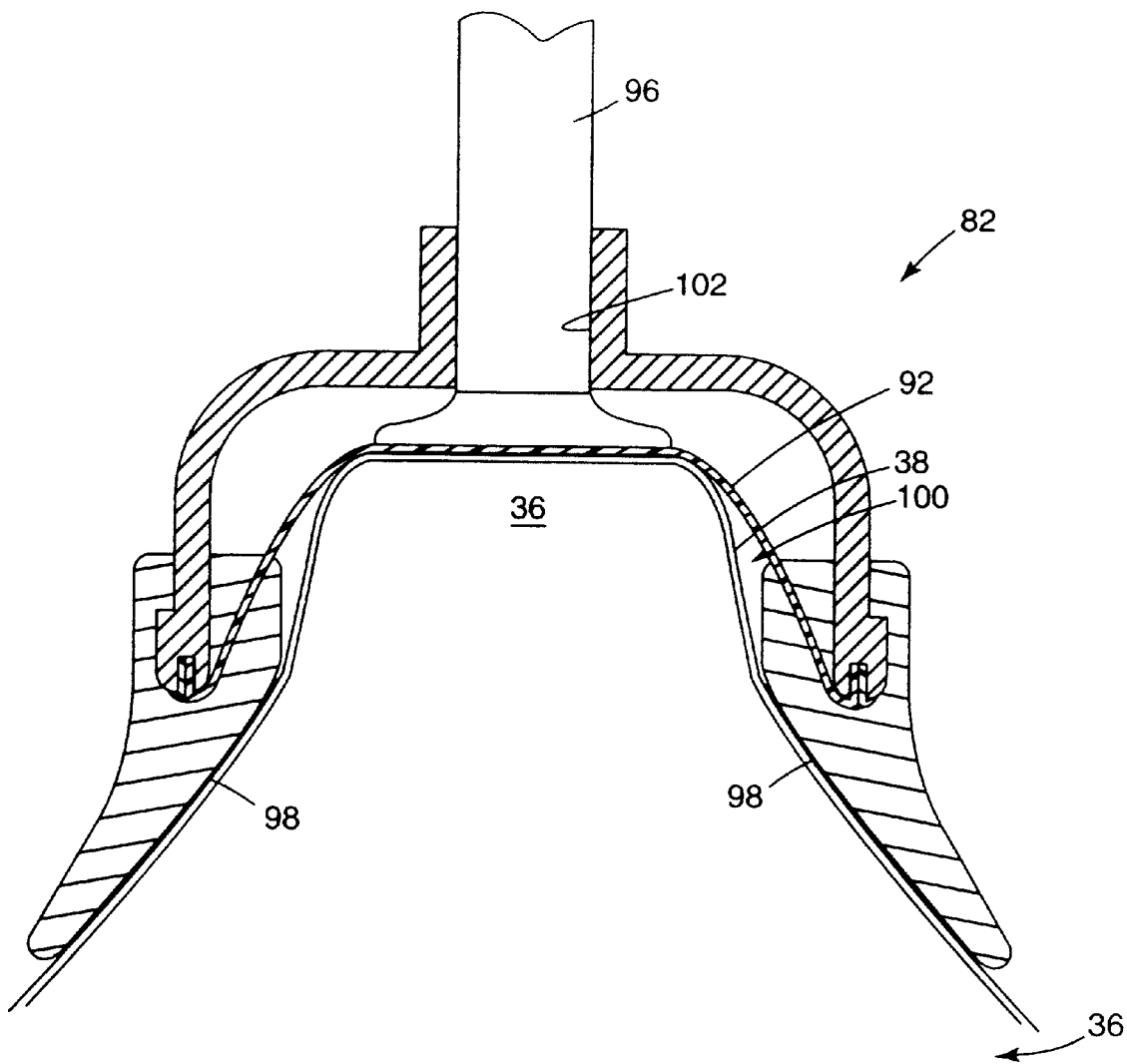
FIG. 7 presents a cross-sectional side view of the embodiment of the invention depicted in FIG. 5, with shaft partially withdrawn and engaging the apex of the heart.

FIG. 7 shows device 82 of FIG. 5 and FIG. 6 in engagement with the apex 38 of a heart 36. Device 82 adheres to the apex 38 in part due to the compliant tacky material 98, upon the extraction of shaft 96 through aperture 102, drawing the tissue into cavity 100. The adherence may be created without a vacuum source, such as a pump or a syringe. In some embodiments, tissue may be drawn into chamber 100 to an extent that the tissue contacts membrane 92.

Figure 8:
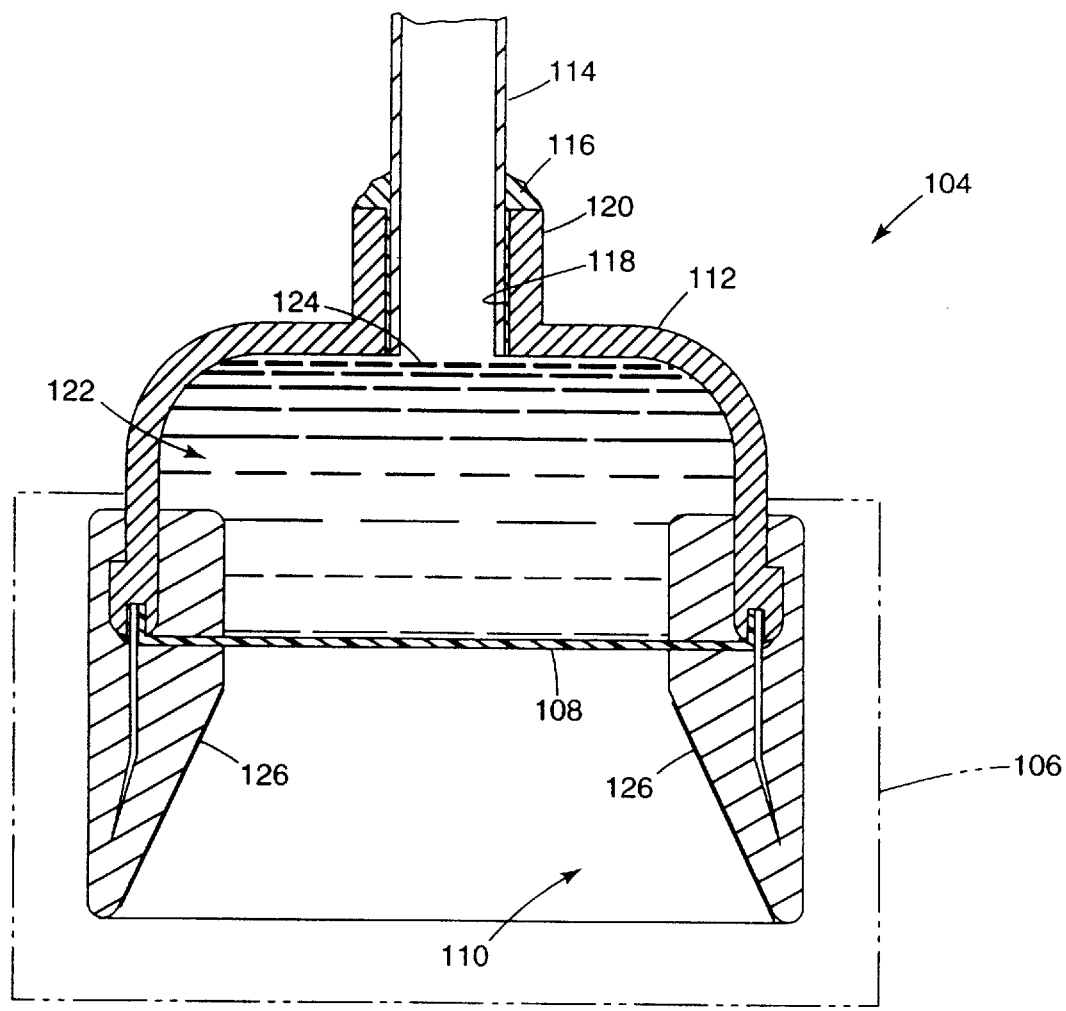
FIG. 8 presents a cross-sectional side view of another embodiment of the present invention.

FIG. 8 is a cross-sectional view of another device 104 for organ manipulation, in accordance with an embodiment of the present invention. Device 104 is similar to device 82 in FIG. 5 in that it includes a membrane 108 preferably manufactured of a flexible airtight and watertight material, affixed at an interface between cup-like member 112 and skirt-like member 106. Cup-like member 112 may include an aperture 118 and a neck 120 suitable for receiving a fluid tube 114. Fluid tube 114 may be sealed in neck 120 with sealant 116.

A first chamber 110 is defined by membrane 108 and skirt-like member 106. A second chamber 122 is defined by membrane 108, the interior surface of cup-like member 112, and fluid tube 114. Second chamber 122 is preferably filled with a liquid 124, such as water or saline solution. When liquid 124 is drawn from device 104 through fluid tube 114, membrane 108 is drawn toward aperture 118, enlarging first chamber 110. Upon engagement with tissue, device 104 may adhere to the tissue in part due to compliant tacky material 126, and in part due to the reduced pressure created within first chamber 110 upon the extraction of liquid 124 through fluid tube 114. Extraction of liquid 124 through fluid tube 114 hydraulically draws the tissue into first cavity 110. A stopping mechanism such as a valve or stopcock (not shown) may be employed to stop the flow of liquid 124 through fluid tube 114, thus promoting adherence by preventing liquid 124 from reentering second chamber 122.

Figure 9:
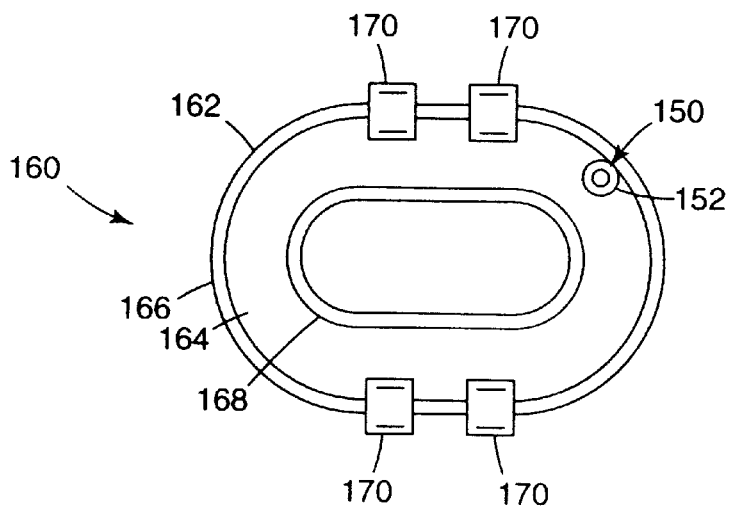
FIG. 9 presents a top view of another embodiment of the present invention.

FIG. 9 is a top view of another device 160 for organ manipulation, in accordance with an embodiment of the present invention. In the embodiment of FIG. 9, the seal member 162 is formed from a structural member 164 and two skirt-like members 166, 168. Structural member 164 defines a size and generally annular shape suitable for forming a ring-like structure. The ring may be of any shape, but the oval shape with a generally oval-shaped inner diameter and a generally oval-shaped outer diameter as shown in FIG. 9 is exemplary. The ring may be generally planar or may be curved to conform to the surface of an organ such as the heart. Seal member 162 may include a vacuum port 150 and a neck 152 suitable for receiving a vacuum tube 154. Vacuum tube 154 may include a valve such as stopcock (not shown) to prevent air from moving through vacuum tube 154, or to allow a quick release of vacuum pressure. Alternatively, a valve may be included in vacuum port 150 or neck 152.

A skirt-like member may be coupled to the inner diameter of the ring, or the outer diameter, or both. In a preferred embodiment, as shown in FIG. 9, an inner skirt-like member 168 is coupled to the inner diameter, and an outer skirt-like member 166 is coupled to the outer diameter.

In addition, structural member 164 provides a firm structure by which the ring-like device 160 may be securely gripped by a surgeon or by an instrument. In FIG. 9, attachments 170 have been affixed to the structural member 164, to provide sites for secure gripping. Attachments 170 may be located elsewhere on the device. A structure such as a handle or a knob may also be suitable for providing a site for secure gripping. Structural member 164 may be molded from many materials, including thermoplastic such as polycarbonate, ABS, polysulfone, polyester and polyurethane, and including corrosion-resistant metals such as titanium, and including rigid, semi-rigid and flexible elastomers such as silicone rubber and polyurethane.

Figure 10:
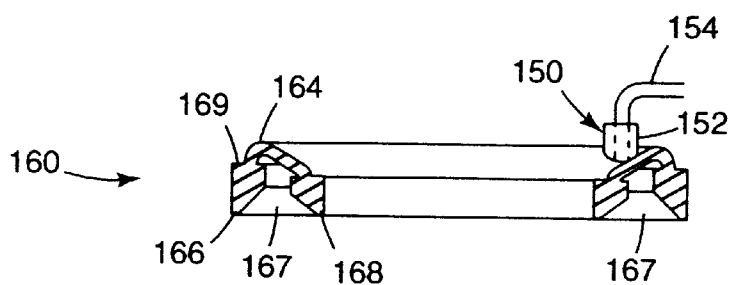
FIG. 10 presents a cross-sectional side view of the embodiment depicted in FIG. 9.

FIG. 10 shows a side view of device 160, which is the same ring-like device as depicted in FIG. 9. Structural member 164 and skirt-like members 166, 168 define a chamber 167 substantially in the shape of a ring. Structural member 164 may also include flanges 169 that aid the physical connection between structural member 164 and skirt-like members 166, 168. Skirt-like members 166, 168 may be reinforced by a reinforcing member (not shown in FIG. 10). FIG. 10 further shows a valve 153 coupled to vacuum tube 154. When device 160 is placed on the surface of tissue such as heart tissue, an external vacuum source can be applied via vacuum tube 154 to remove air from inside device 160. When valve 153 is closed, atmospheric pressure holds device 160 to the tissue, and the external vacuum source can be removed. No additional external vacuum source is then required. Tacky material 174 shown in FIG. 11 helps promote adhesion to the tissue, and compliant skirt-like member 171 conforms to the shape of the tissue to create an airtight seal.

Figure 11:
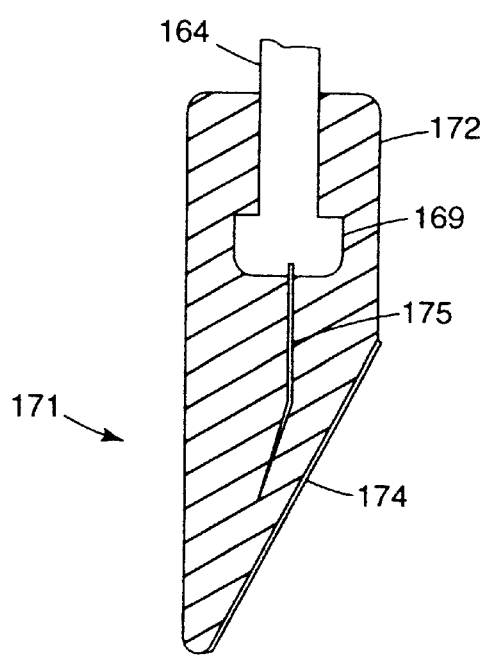
FIG. 11 presents a close-up cross-sectional view of a portion of a skirt-like member as depicted in FIG. 10.

FIG. 11 presents a cross-sectional view of a typical skirt-like member 171 for device 160 of FIG. 9. Skirt-like member 171 may be an inner skirt-like member or an outer skirt-like member. Skirt-like member 171 includes a main ring 172, coupled to structural member 164 around flange 169. Furthermore, skirt-like member 171 may be reinforced with a reinforcing member 175, similar to reinforcing member 30 shown in FIG. 1. Reinforcing member 175 may be partly embedded within the main ring 172 and anchored within flange 169 of structural member 164. One embodiment of reinforcing member 175 is a spring or wire or shape-memory metal that generally resists deformation, like reinforcing member 30 shown in FIG. 1.

Skirt-like member 171 may include a tacky inner layer 174 bonded to the main ring member 172. Main ring member 172 may be formed from silicone gel in approximately the ratios described above for main ring 28 in FIG. 1. Tacky inner layer 174 may be formed from silicone gel in approximately the ratios described above for tacky material 34 in FIG. 1.

Figure 12:
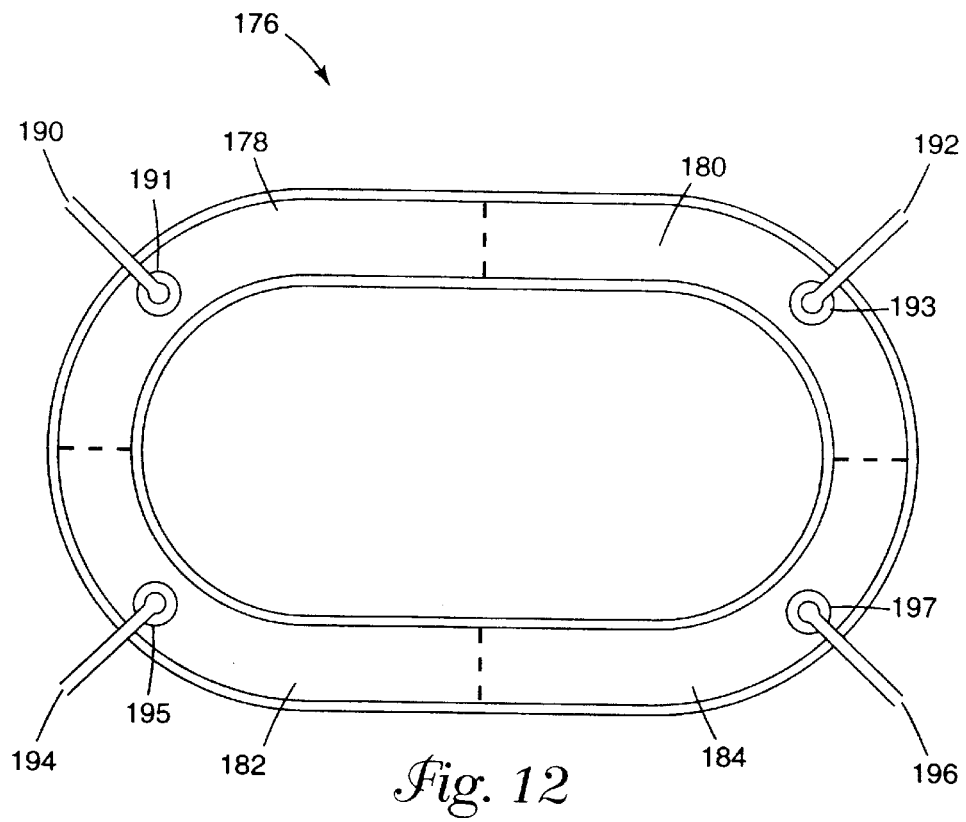
FIG. 12 presents a top view of another embodiment of the present invention.

FIG. 12 is a top view of another device 176 for organ manipulation, in accordance with an embodiment of the present invention. Although similar in overall shape and construction to the device 160 shown in FIG. 9, device 176 shown in FIG. 12 has multiple chambers 178, 180, 182, 184, each in fluid contact with vacuum lines 190, 192, 194, 196 via vacuum ports 191, 193, 195, 197. No chamber is in fluid contact with any other chamber. The vacuum pressure within each chamber may be created separately and independently from the other chambers, by means such as a syringe or vacuum pump (not shown). Moreover, the vacuum pressure within each chamber may be maintained separately and independently from the other chambers, by means such as a valve or stopcock (not shown). The advantage of device 176 is that each chamber is vacuum sealed independent of the others. A rupture a seal of one chamber will not necessarily cause a loss of vacuum pressure throughout the device 176. In this way, device 176 may continue to adhere to the tissue even if the vacuum seal is ruptured at a site and vacuum pressure within one chamber is lost.

Figure 13:
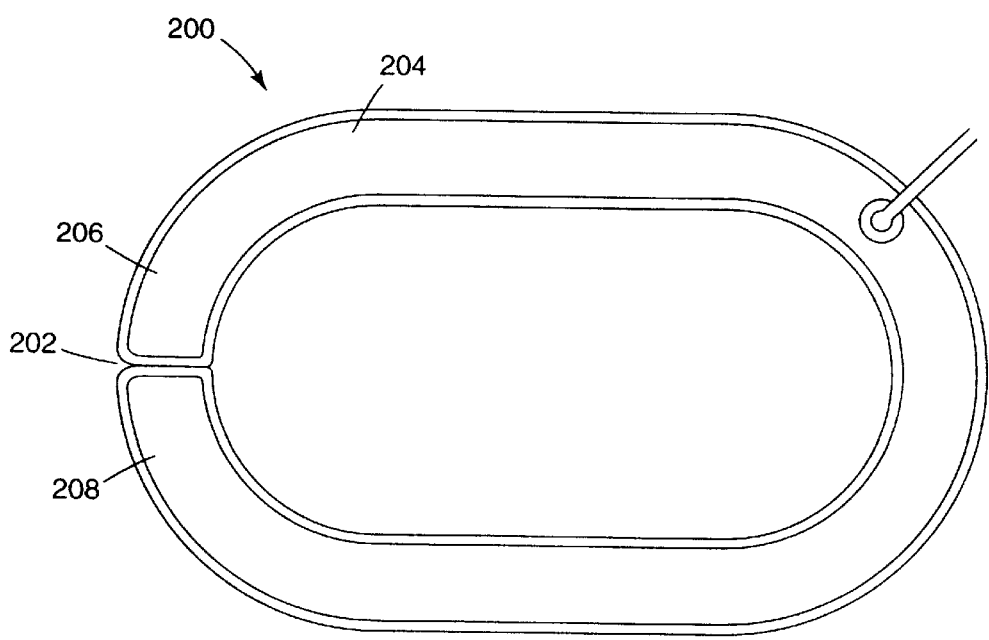
FIG. 13 presents a top view of another embodiment of the present invention.

FIG. 13 is a top view of another device 200 for organ manipulation, in accordance with an embodiment of the present invention. Although similar in overall shape and construction to the device 160 shown in FIG. 9, device 200 shown in FIG. 13 has a chamber 204 presented in a general C-shape instead of a ring. A gap 202 separates the two tines or "feet" 206, 208 of the device. The C-shape may vary in shape and dimension, but the near-oval shape with a generally oval-shaped inner diameter and a generally oval-shaped outer diameter as shown in FIG. 13, is exemplary. Gap 202 may also vary in size, such that the feet 206, 208 need not touch each other, and device 200 could assume a general U-shape.

Figure 14:
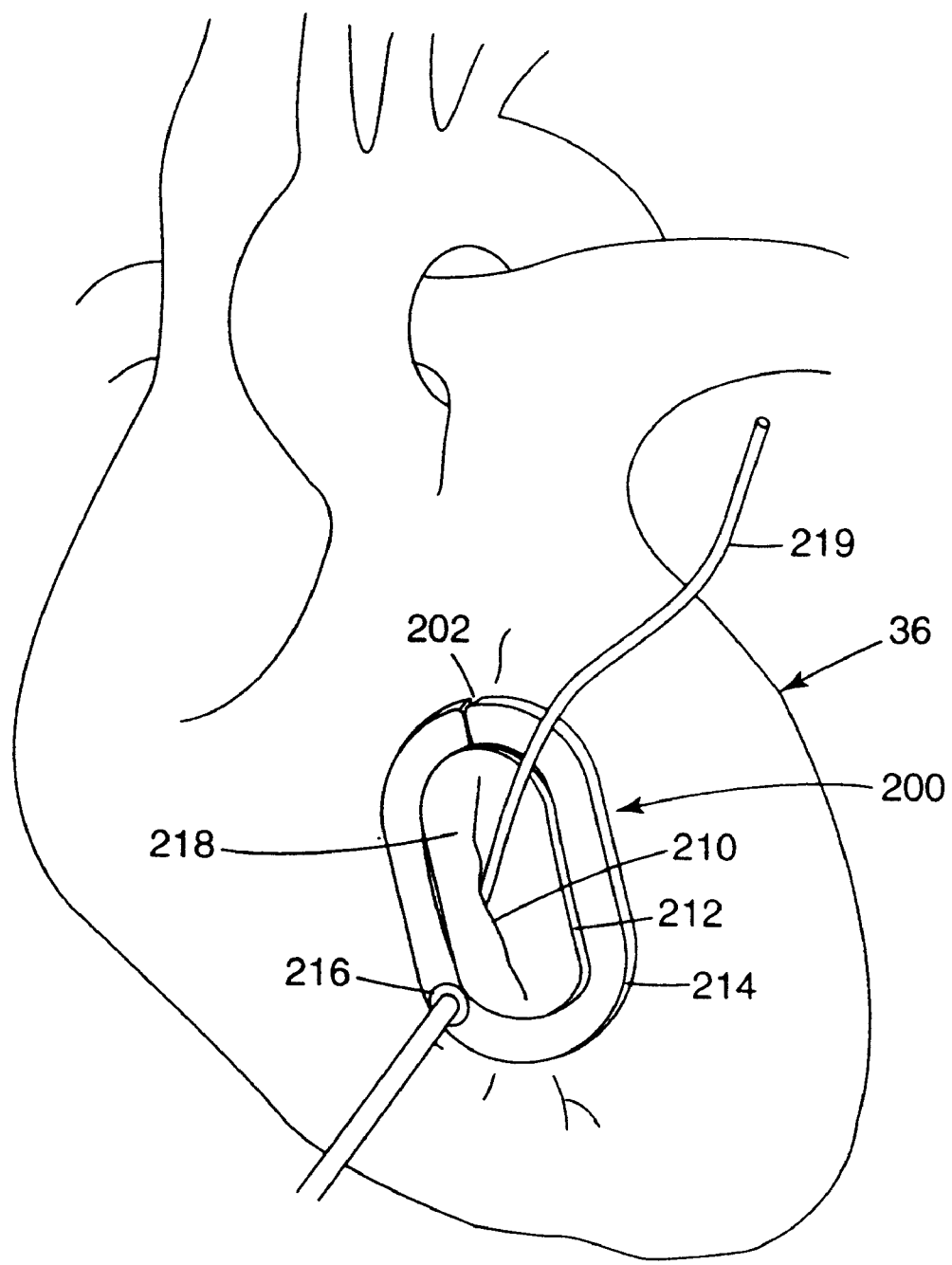
FIG. 14 presents a perspective view of an embodiment of the invention as depicted in FIG. 13, applied to the heart.

FIG. 14 shows the device 200 of FIG. 13 in an exemplary application. Device 200 had been placed so that a vessel 210 on the surface of the heart 36 has been centered within the C-shape. The skirt-like members 212, 214, which are like skirt-like member 171 shown in FIG. 11, assist in providing adhesion to the desired site. Vacuum pressure had been applied through the vacuum port 216 to provide additional adherence to the surface of the heart 36. With the device adhered to the heart 36, the inner diameter of the device 200 forms a field 218 for the surgeon. Within field 218, the contractions of the heart 36 may be reduced, although the heart 36 continues to beat, providing a tissue stabilizing effect. The surgeon may access the vessel 210 within the field 218, without arresting the heart 36.

In the course of the operation depicted in FIG. 14, an item may be applied to vessel 210 within field 218. For example, vessel 210 or other tissue within field 218 may be seized by a medical instrument such as a hemostat. Or a surgeon may perform a vascular graft in which a vessel from another area of the body 219 is physically attached to vessel 210, perhaps bypassing a blockage in vessel 210 and supplying blood to regions of the heart 36 normally supplied by vessel 210. In cases such as these, it may be desirable to remove device 200 without disturbing other items within the field such as vessel 219. The C-shape configuration of device 200 may allow device 200 to be removed from the heart, by separating the gap 202 and maneuvering device 200 around the other items.

Figure 15:
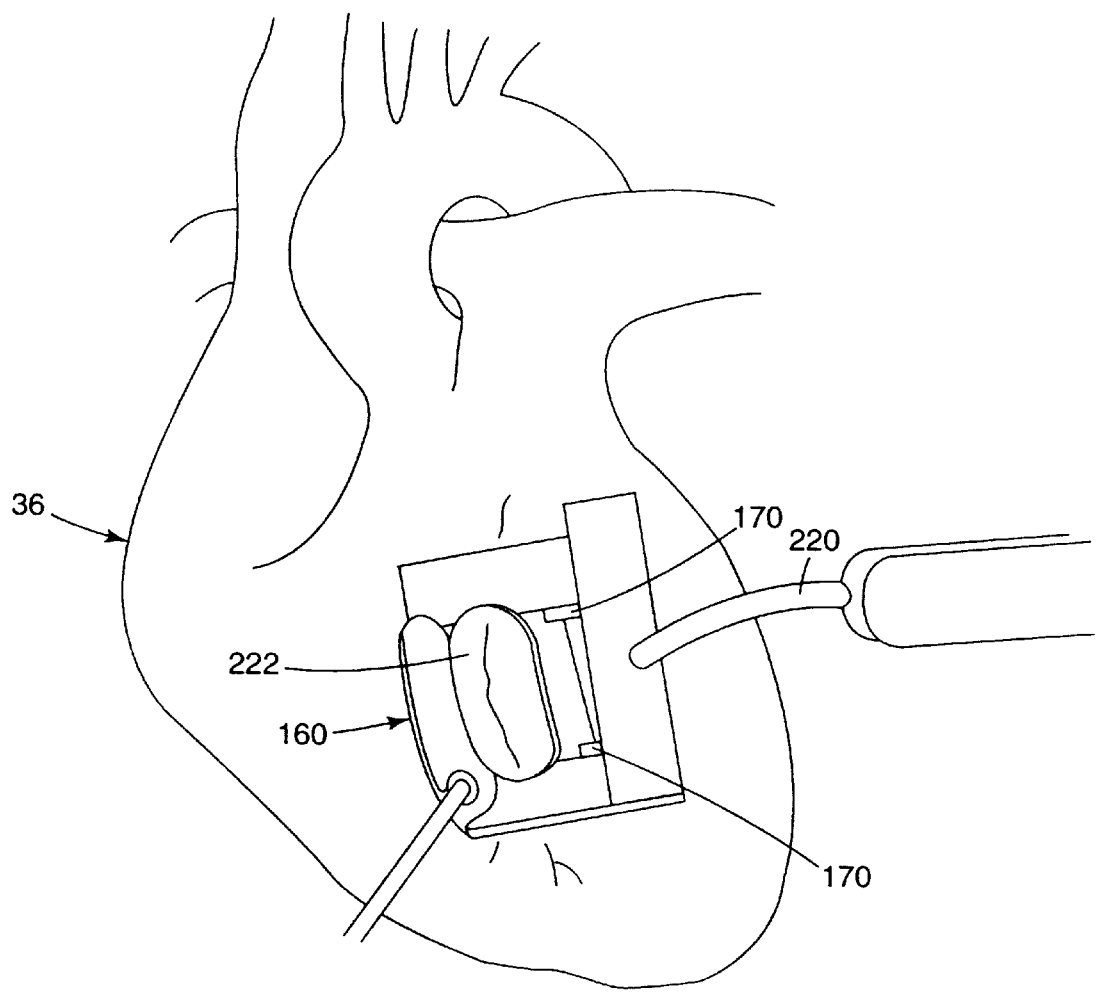
FIG. 15 presents a perspective view of an embodiment of the invention as depicted in FIG. 9, applied to the heart.

FIG. 15 shows an exemplary application of device 160 shown in FIG. 9. Device 160 in FIG. 15 is held by a securing device 220 at attachment points 170. Securing device 220 may in turn be affixed to a relatively immobile object, such as a rib spreader (not shown) or an operating table (not shown). The advantage of this arrangement is that the field 222 is substantially immobile relative to the rest of the heart 36, which continues to beat, and substantially immobile relative to the patient.

Figure 16:
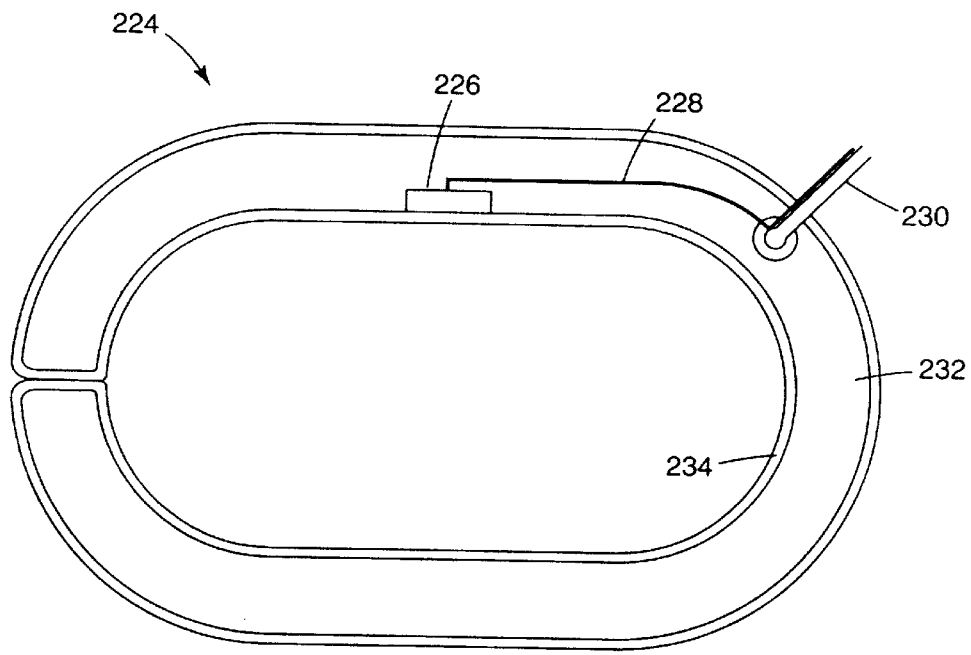
FIG. 16 presents a top view of another embodiment of the present invention.

FIG. 16 is a top view of another device 224 for organ manipulation, in accordance with an embodiment of the present invention. Device 224 is similar in overall shape and construction to the device 200 shown in FIG. 13, and further includes a first electrode 226. First electrode 226 is connected to a power supply (not shown) via wire 228 that may follow the same path as vacuum tube 230. First electrode 226 may be affixed to another element of device 224 at various locations. First electrode 226 may be attached to or partly incorporated within chamber 232, for example, or attached to or partly incorporated within a skirt-like member 234. First electrode 226 ordinarily would be located such that electrode 226 would come in contact with tissue when device 224 is engaged against the tissue. A second matching electrode, connected to the same power supply, may be attached to a scalpel (not shown). Such an arrangement of electrodes may be useful for bipolar surgery, in which electric current is a part of the procedure. During bipolar surgery, current passing between the second scalpel electrode and the first electrode 226 on device 224 may serve to provide immediate cauterization to an incision.

Figure 17:
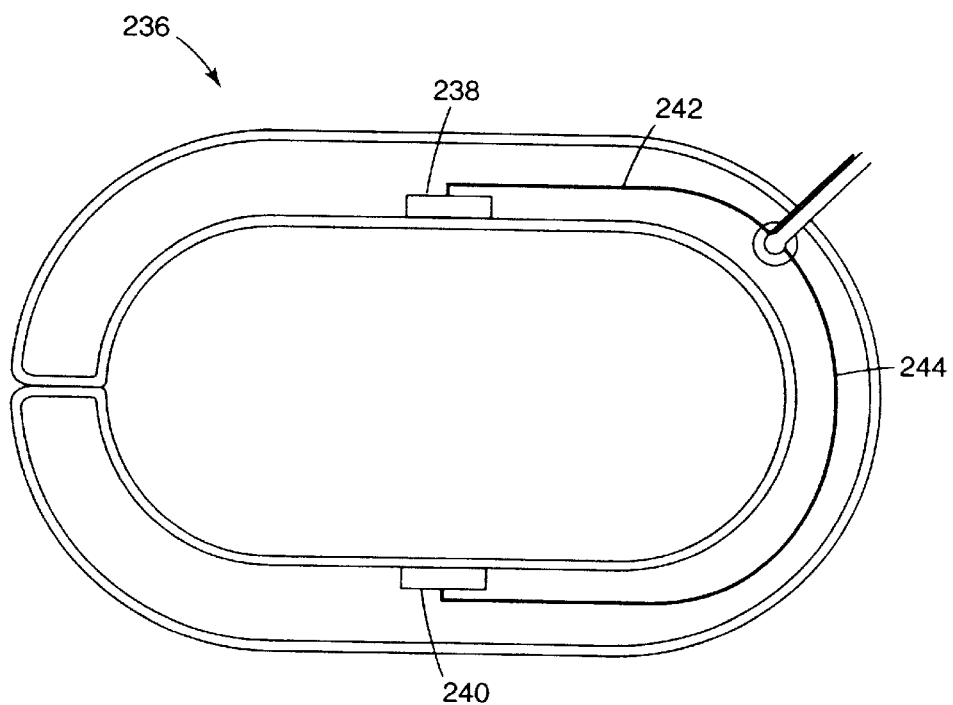
FIG. 17 presents a top view of another embodiment of the present invention.

FIG. 17 is a top view of another device 236 for organ manipulation, in accordance with an embodiment of the present invention. Device 236 is similar in overall shape and construction to the device 224 shown in FIG. 16. Like device 224 shown in FIG. 16, device 236 includes a first electrode 238. In FIG. 17, however, second electrode 240 is included within device 236, rather than within another surgical instrument. Both electrodes 242, 244 preferably come in contact with tissue when device 236 is engaged against the tissue. Electrodes 238, 240 may be connected to associated circuitry by wires 242, 244. In device 236, first electrode 238 may be capable of sending electrical signals, and second electrode 240 may be capable of substantially receiving the electrical signals sent by first electrode 238. Such an arrangement of electrodes may be useful in many kinds of surgical procedures, such as those in which electric current is a part of the procedure. In accordance with the present invention, a surgeon may, for example, wish to measure the impedance or other characteristics of the tissue between the electrodes, or the time needed for an electrical signal to conduct along the tissue. Further, the electrodes may be connected to an external pulse generator and be useful in pacing the heart.

Figure 18:
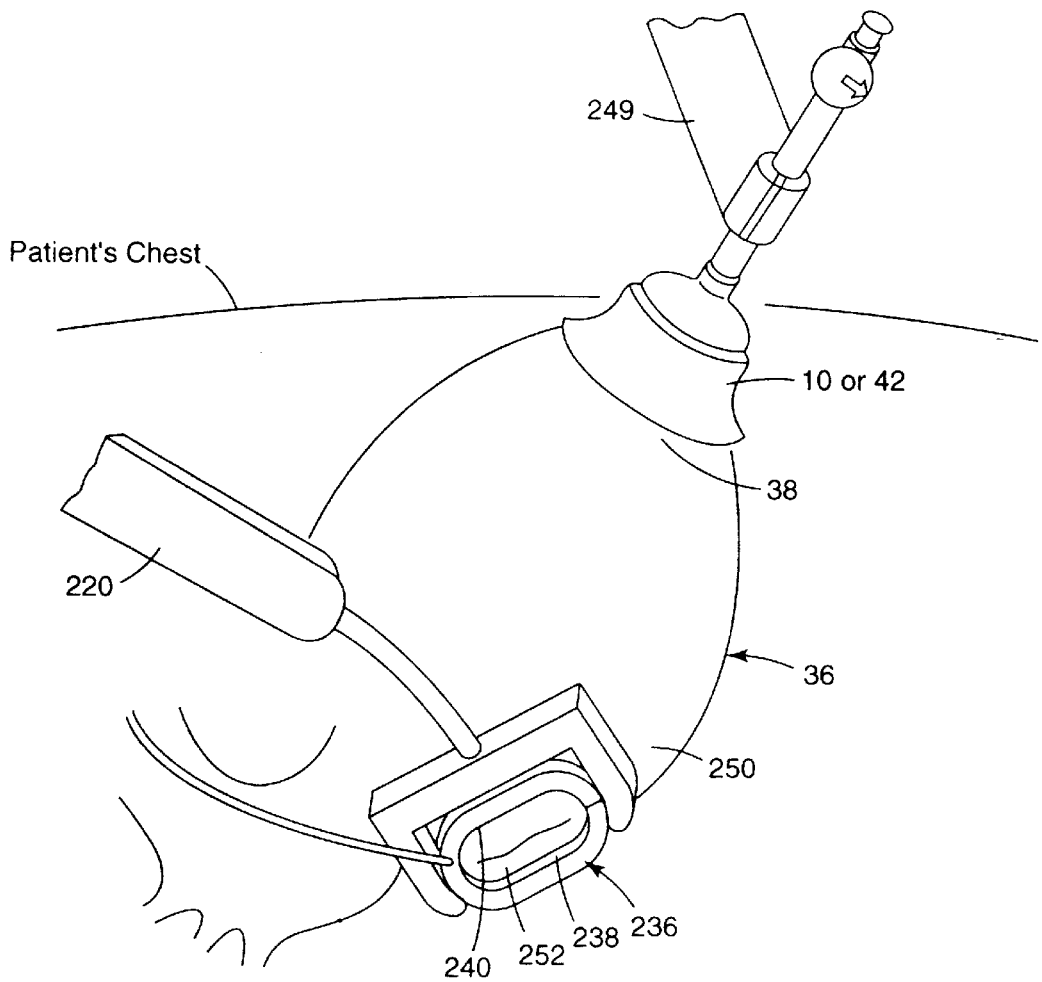
FIG. 18 presents a perspective view of the embodiment of the invention depicted in FIG. 1 and the embodiment of the invention depicted in FIG. 17, applied to the heart.

FIG. 18 provides a perspective view of two embodiments of the present invention, in two contemporaneous exemplary applications. One embodiment of the invention is a cup-shaped device 10, like the device shown in FIG. 1 or other embodiments such as 42, 82, 104, 280. Another embodiment is a C-shaped device 236, as shown in FIG. 18. Both devices 10, 236 have been applied to the heart 36 at the same time. In FIG. 18, cup-shaped device 10 has been adhered to the apex 38 of the heart 36, in a manner like that depicted in FIG. 2. By manipulation of apex 38, a surgeon can lift or turn the heart 36 to obtain access to areas of the organ not easily accessible. The surgeon may then immobilize device 10 by securing it to a securing device 249. When positioned appropriately device 10 may be further immobilized by attaching the securing device 249 to either the rib expander or the operating table. In FIG. 18, the heart 36 has been lifted and turned to allow access to a region of the right atrium 250. C-shaped device 236 has been applied to the atrium 250 in a manner similar to that shown in FIG. 14. Engagement of C-shaped device 236 may stabilize the tissue within field 252, relative to the rest of the heart. By further affixing device 236 to a securing device 220 which is in turn attached to either a rib expander or the operating table. Having obtained access to the right atrium 250, the surgeon may perform an operation in the field 252. For example, the surgeon may use an ablation probe to ablate tissue within the field 252, and sever pathways of electrical conduction. Such a severing may be helpful, for example, as a treatment for a kind of arrhythmia. To determine whether the pathways have been properly severed, the surgeon may measure a quantity such as conduction time or impedance using electrodes 238, 240.

Figure 19:
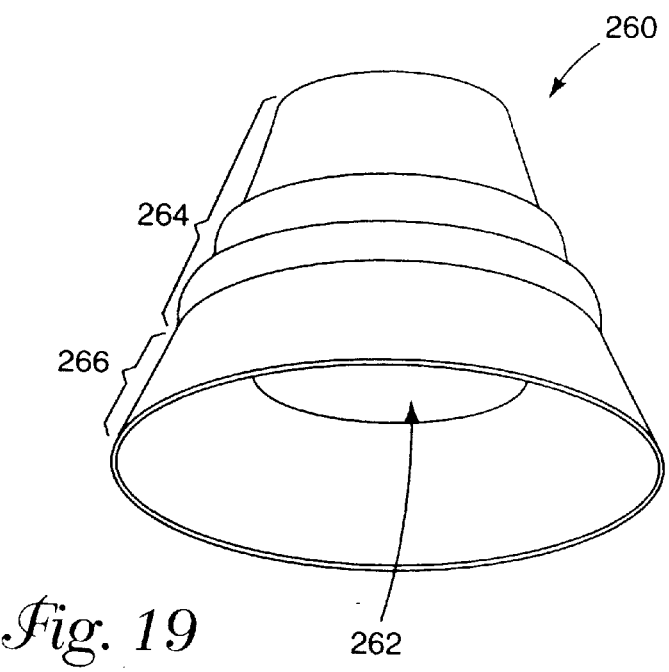
FIG. 19 is a perspective view of a cup-like seal member according to another embodiment of the present invention.
Figure 20:
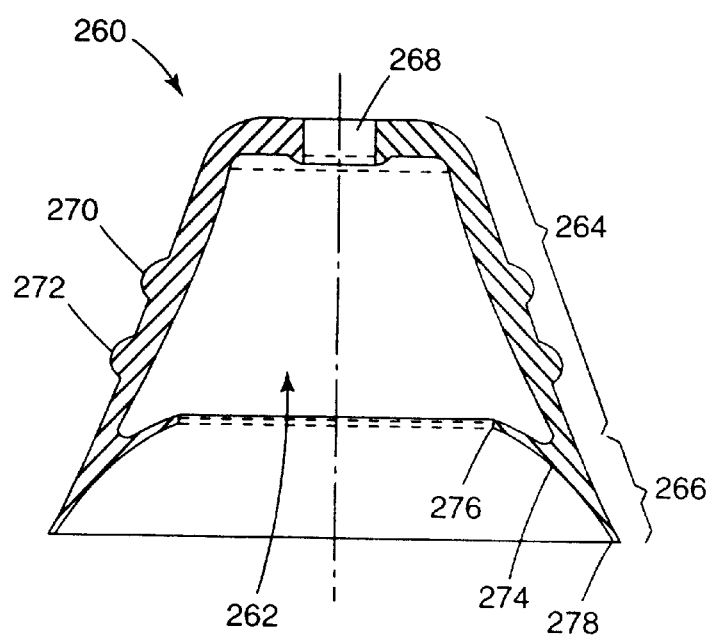
FIG. 20 is a cross-sectional side view of the seal member of FIG. 19.

FIG. 19 is a perspective view of a cup-like seal member 260 according to another embodiment of the present invention. FIG. 20 is a cross-sectional side view of the seal member of FIG. 19. As shown in FIG. 19, seal member 260 may be somewhat similar to other seal members described above in that it defines an inner chamber 262 for application of vacuum pressure and affixation to the surface of the heart. Seal member 260 may have an upper portion 264 formed form a semi-rigid material, e.g., a silicone elastomer of Shore A 30 to 70 durometer. A lower skirt-like member 266 may be coupled to or molded with upper portion 264, and may be formed from a substantially compliant material, such as a silicone elastomer of Shore A 5 to 10 elastomer. Alternatively, skirt-like member 266 may be formed from a silicone gel that is both compliant and tacky, enhancing sealing pressure. As mentioned above, the MED 6340 silicone gel material available from Nu-Sil may be acceptable for fabrication of skirt-like member 266. Seal member 260 may include a vacuum port 268 for communication with a vacuum tube and an external vacuum source. Also, seal member 260 may include two exterior circumferential ribs 270, 272 that can be molded into upper portion 264. Ribs 270, 272 provide seal member 260 with added strength to prevent collapse under vacuum pressure and consequent failure of the seal. As will be explained, skirt-like member 266 provides a canted surface 274 that promotes sealing on both the inner and outer diameters 276, 278 of the skirt-like member.

Figure 21:
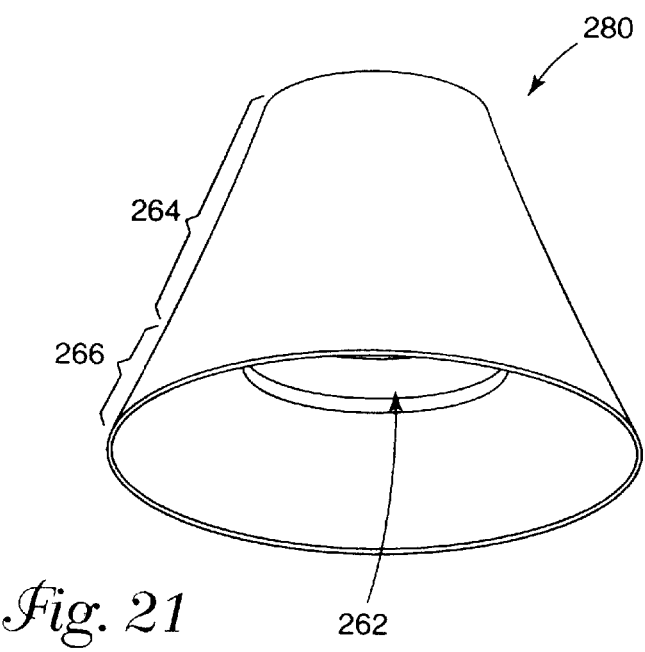
FIG. 21 is a perspective view of a cup-like seal member according to another embodiment of the present invention.
Figure 22:
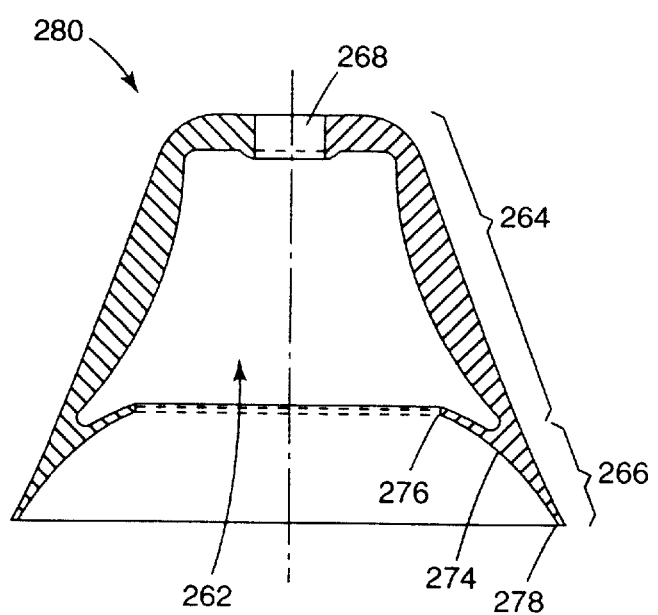
FIG. 22 is a cross-sectional side view of the seal member of FIG. 21.

FIG. 21 is a perspective view of a cup-like seal member 280 according to another embodiment of the present invention. FIG. 22 is a cross-sectional side view of the seal member 280 of FIG. 21. Seal member 280 corresponds to seal member 260 of FIG. 19 but omits circumferential ribs 270, 272.

Figure 23:
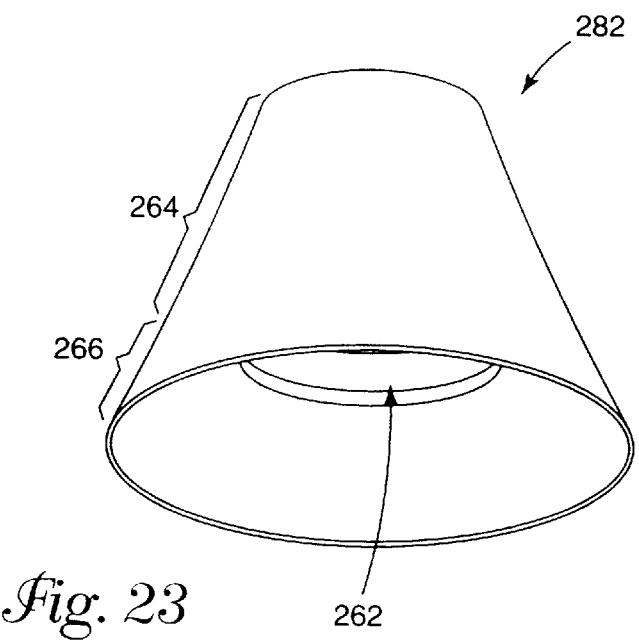
FIG. 23 is a perspective view of a cup-like seal member according to another embodiment of the present invention.
Figure 24:
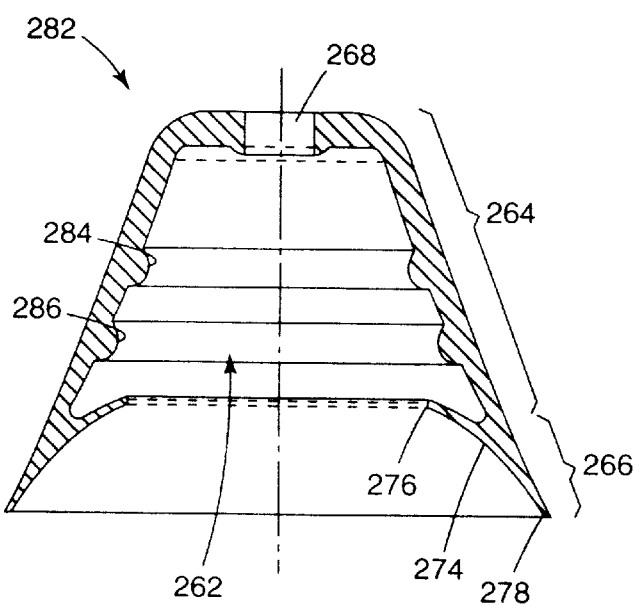
FIG. 24 is a cross-sectional side view of the seal member of FIG. 23.

FIG. 23 is a perspective view of a cup-like seal member 282 according to another embodiment of the present invention. FIG. 24 is a cross-sectional side view of the seal member 282 of FIG. 23. Seal member 282 corresponds to seal member 280 of FIG. 21 but incorporates internal circumferential ribs 284, 286.

Figure 25:
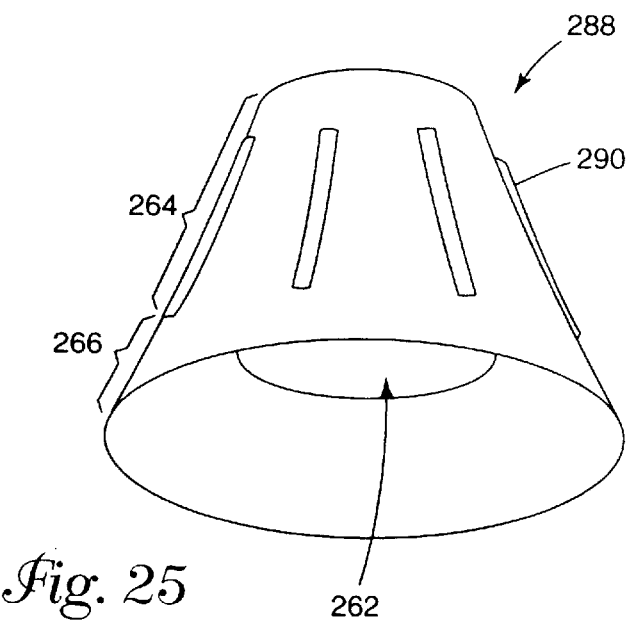
FIG. 25 is a perspective view of a cup-like seal member according to another embodiment of the present invention.
Figure 26:
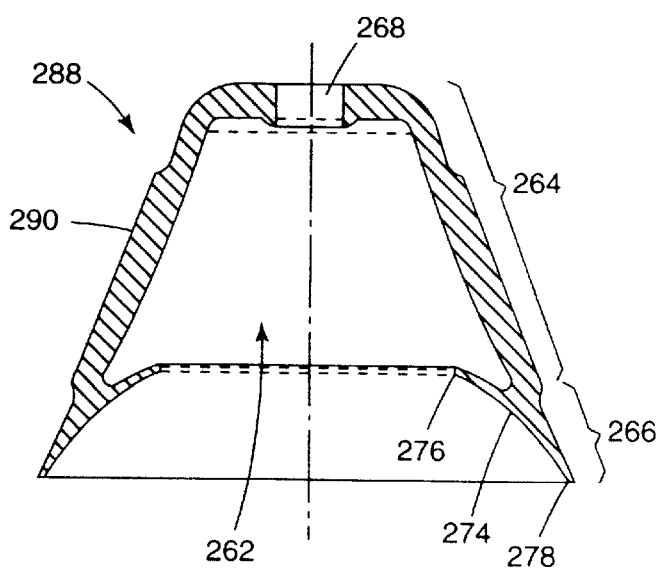
FIG. 26 is a cross-sectional side view of the seal member of FIG. 25.

FIG. 25 is a perspective view of a cup-like seal member 288 according to another embodiment of the present invention. FIG. 26 is a cross-sectional side view of the seal member 288 of FIG. 25. Seal member 288 corresponds to seal member 260 of FIG. 19 but instead of circumferential ribs 284, 286, incorporates external vertical ribs 290.

Figure 27A:
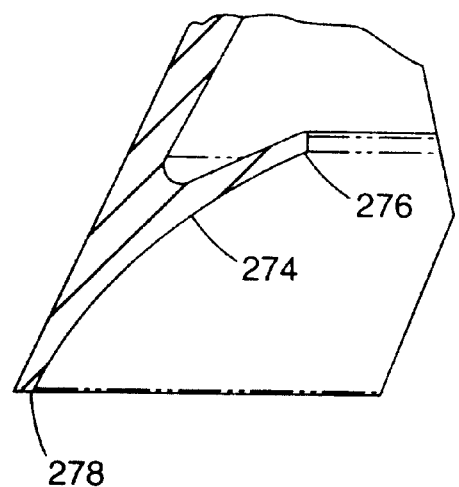
FIG. 27a is an enlarged view of a skirt member associated with a seal member as shown in any of FIGS. 19–26.
Figure 27B:
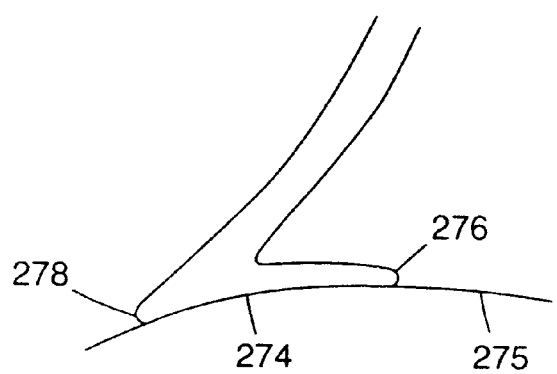
FIG. 27b shows the skirt member of FIG. 27a in use.

FIG. 27a is an enlarged partial view of a skirt member associated with a seal member as shown in any of FIGS. 19–26. When vacuum pressure is applied to the respective seal member, the conformable canted surface 274 gives way and flexes inward and downward such that it contacts the tissue at both inner diameter 276 and outer diameter 278, producing greater surface contact area, and promoting an effective seal. FIG. 27b illustrates canted surface 274 upon application to a tissue surface 275.

Figure 28:
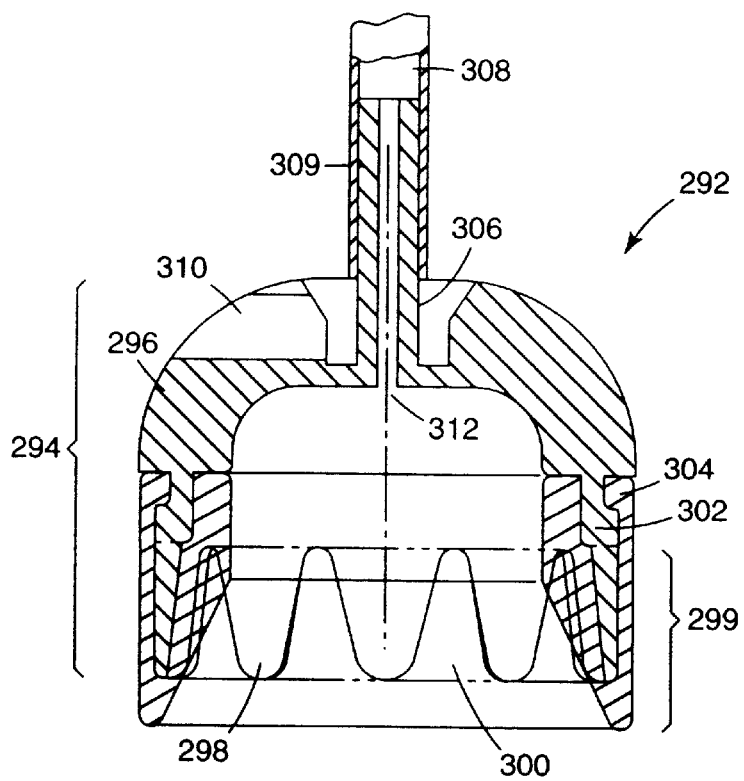
FIG. 28 is a side view of a seal member incorporating a reinforcing structure and a swivel connection in accordance with a further embodiment of the present invention.
Figure 29:
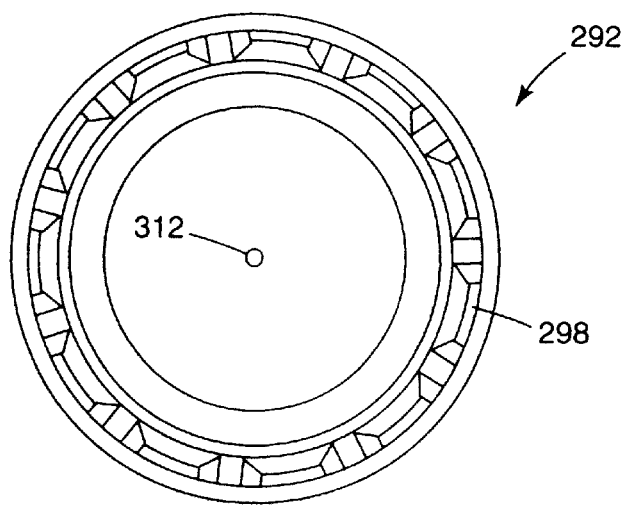
FIG. 29 is bottom view of the seal member of FIG. 28.
Figure 30:
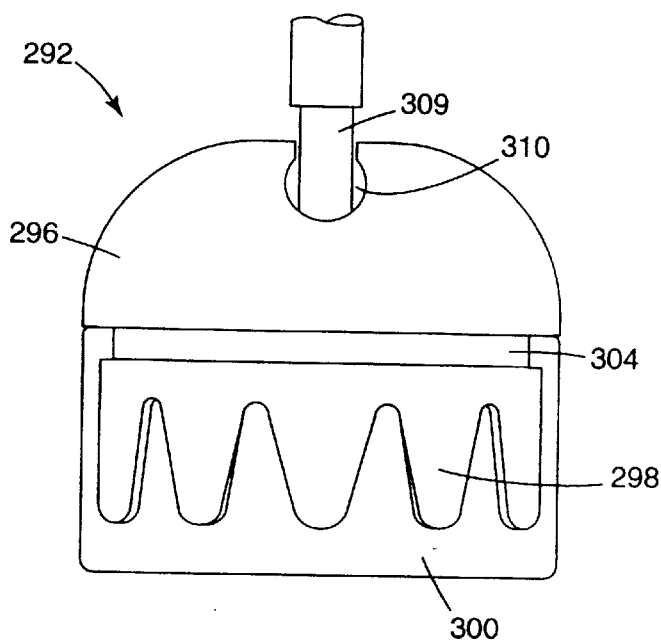
FIG. 30 is another side view of the seal member of FIG. 28.
Figure 32:
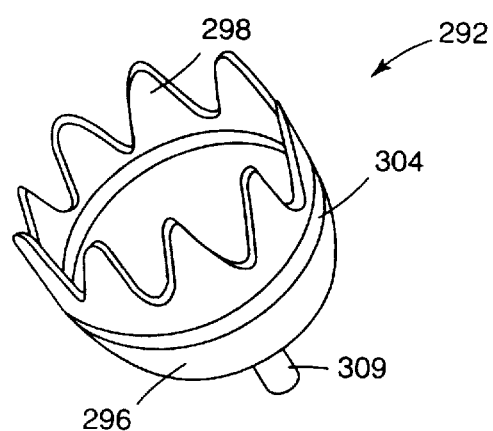
FIG. 32 is a bottom perspective view of the seal member of FIG. 28.
Figure 31:
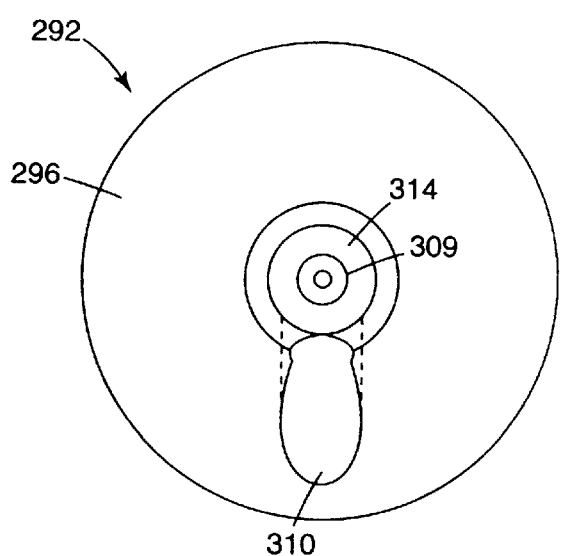
FIG. 31 is a top view of the seal member of FIG. 28.

FIG. 28 is a side view of a seal member 292 incorporating a reinforcing structure and a swivel connection in accordance with a further embodiment of the present invention. FIG. 29 is bottom view of the seal member 292 of FIG. 28. FIG. 30 is another side view of the seal member 292 of FIG. 28. FIG. 31 is a top view of the seal member 292 of FIG. 28. FIG. 32 is a bottom perspective view of the seal member 292 of FIG. 28. As shown, seal member 292 includes an upper portion 294 defining a semi-rigid cup-like member 296 with a set of finger-like extensions 298. Molded around extensions 298 is a lower portion 299 having a compliant skirt-like member 300. Cup-like member 296 may be formed from a variety of materials such as silicone elastomers in the range of Shore A 30 to 70 durometer. Extensions 298 may be integrally formed with cup-like member 296 by molding. Skirt-like member 300 may extend below extensions 298 to a lip 302 and just above the extensions to a channel indicated by reference numeral 304. Extensions 298 may thin in both thickness and width as they approach the lower extent of skirt-like member 300. Extensions 298 provide added support to seal member 292, helping to resist collapse under vacuum pressure. Skirt-like member 300 may be formed from a substantially compliant material, such as a silicone elastomer of Shore A 5 to 10 elastomer. Alternatively, skirt-like member 300 may be formed from a silicone gel such as Nu-Sil MED 6340 that is both compliant and tacky, enhancing sealing pressure.

Seal member 292 also may include a swivel-mount 306 designed to receive a vacuum tube 308. Swivel 306 may take the form of an extension or "stem" 309 that can be bonded inside a stainless steel tube 308. Seal member 292 defines a "notch-out" area 310 that accommodates the tube when the tube is bent relative to the seal member, e.g., at 90 degrees. In this manner, vacuum tube 308 can be bent relative to seal member 292 to permit positioning of the seal member over the apex of the heart while the vacuum tube is held by the surgeon at an angle to the apex. Stem 309 is inserted into vacuum port 312, which is positioned within a recess 314. Cup recess area 314 may have a width sufficient to permit swiveling of seal member 292 approximately 30 degrees relative to the longitudinal axis of stem 309.

This design may provide a number of advantages. In particular, seal member 292 may be relatively simple to construct and reconstruct. The swivel capability permits the heart to twist and slightly bob with each beat while seal member 292 is affixed to the apex. Also, the seal member 292 is able to self-center on the apex by reducing side bending moments. Further, seal member 292 can be oriented at 90 degrees relative to the vacuum tube with the vacuum tube residing in notch-out area 310 to permit it to be mounted on the apex without heart manipulation. To lift the heart, the vacuum tube then gradually moves out of notch-out area 310. As in other embodiments, seal member 292 and, in particular, skirt-like member 300 may incorporate electrodes and conductors for pacing or diagnosis.

Figure 33:
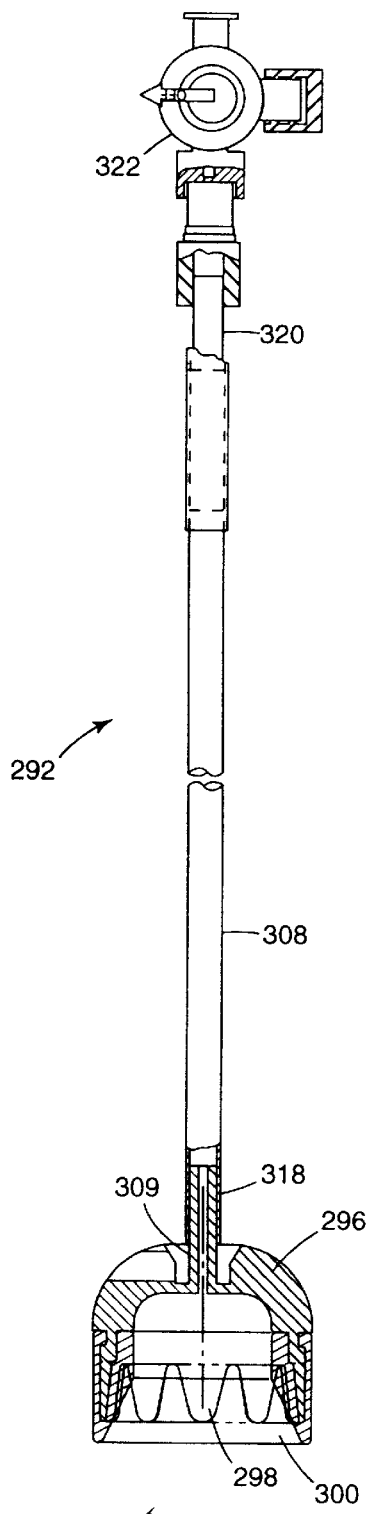
FIG. 33 is a side view of a device incorporating a seal member as shown in FIG. 28.

FIG. 33 is side view of a device incorporating a seal member as shown in FIG. 28. As shown in FIG. 33, seal member 292 may be coupled to a length of vacuum tubing 308 having a distal end 318 at seal member 292 and a proximal end 320 at a valve device 322 coupled to a vacuum source.

Figure 34:
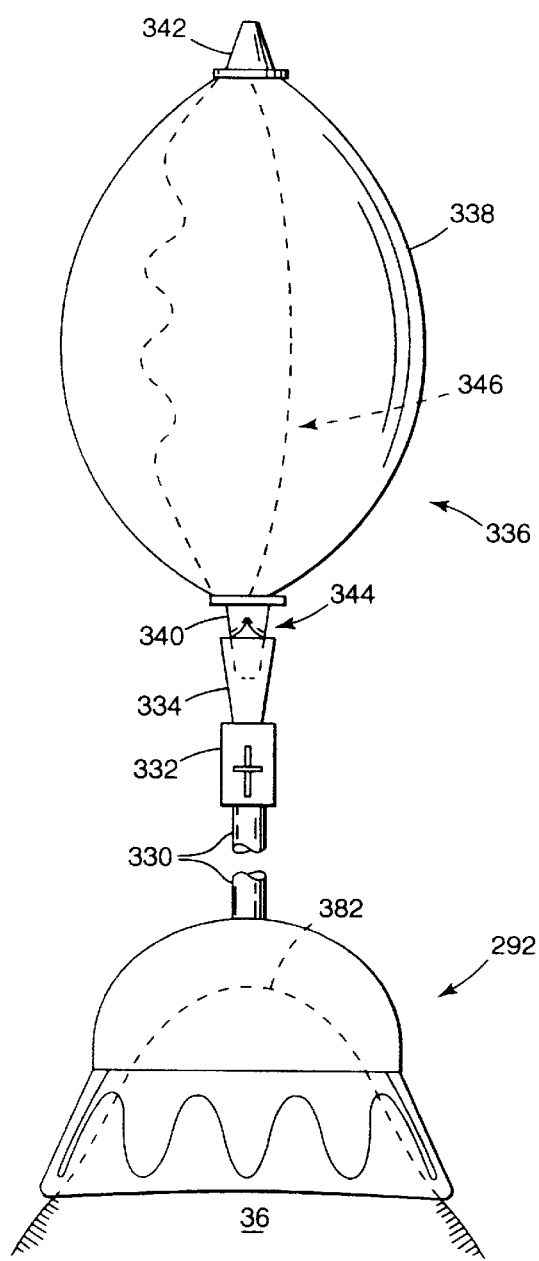
FIG. 34 is a side view of a device incorporating a seal member as shown in FIG. 28 and showing a flexible bulb.

FIG. 34 is a side view of a device incorporating a seal member as shown in FIG. 28. The seal member 292 is engaged to the apex 38 of a heart 36. The seal member 292 is coupled to vacuum tubing 330. Vacuum tubing includes or is coupled to a manually-operable valve 332, and is further equipped with a fitting 334 such as a Luer fitting. A pressure device 336 is coupled to the fitting 334. The pressure device 336 shown in FIG. 34 includes a flexible bulb 338, an inlet valve 340 and an exhaust valve 342. The bulb 338 may be constructed of material such as rubber or an elastic polymer, and is biased to resume its shape after deformation. The inlet valve 340 is configured to allow fluid flow into the bulb 338, but internal valve opening 344 is biased to prevent fluid flow out of the bulb 338 through the inlet valve 340. Exhaust valve 342, by contrast, is configured to allow fluid flow out of the bulb 338, but is biased to restrict or prevent fluid flow into the bulb 338.

When the bulb 338 is compressed 346, air is ejected through the exhaust valve 342. When the bulb 338 is released, the internal volume of the bulb 338 begins to expand as the bulb returns to its undeformed shape. As the internal volume of the bulb 338 expands, the bulb 338 draws air through the inlet valve 340, creating a partial vacuum between the seal member 12 and the heart 36. The partial vacuum may cause the seal member 292 to deform to create a more robust seal with the myocardial tissue. When the partial vacuum is created, the manually-operable valve 332 may be closed, thus maintaining the partial vacuum. The heart 36 may then be manipulated by moving the device 292 or the vacuum tube 330. An advantage of a fitting 334 such as a Luer fitting is that the pressure device 336 may be quickly uncoupled from the fitting 334. An additional advantage of a Luer fitting is that the pressure device 336 may quickly be reversed, and the exhaust valve 342 coupled to the fitting 334. In this configuration, with manually-operable valve 332 opened, compression of the bulb 338 forces air through tube 330 to facilitate rapid detachment of device 292 from heart 36.

FIG. 34 shows one embodiment of a detachable pressure device 336. Other forms of pressure devices include various forms of pumps, such as syringes or bellows. Because negative pressure can be preserved by closing valve 332 and because seal member 292 does not require a continuous source of negative pressure to adhere to apex 38, the source of the vacuum or pressure device 336 may be detached without compromising adherence. Detachability of pressure device 336 from vacuum tube 330 is useful because the source may be removed from the surgical field so it will not interfere with the surgery.

Although FIG. 34 shows pressure device 336 used with seal member 292, pressure device 336 may be used with other embodiments of the invention described above.

The details of one or more embodiments of the invention are set forth in the accompanying drawings and the description below. Other features, objects, and advantages of the invention will be apparent from the description and drawings, and from the claims.

What is claimed is:

1. An organ manipulation device comprising:
 a seal member having a wall defining a chamber and a skirt-like member that extends outward from the wall for contact with a surface of an organ;
 a fluid tube in fluid communication with the interior of the chamber; and
 a valve to regulate fluid flow through the fluid tube.

2. The device of claim 1 further comprising a source of pressure coupled to the fluid tube configured to move fluid through the fluid tube.

3. The device of claim 2 wherein the source of pressure is one of a pump, syringe or flexible bulb.

4. The device of claim 1 wherein the fluid is air.

5. The device of claim 1 further comprising a flexible, watertight membrane affixed between the wall and the skirt-like member.

6. The device of claim 5 wherein the fluid is a hydraulic fluid.

7. The device of claim 1 wherein the skirt-like member is substantially compliant and tacky, thereby promoting adhesion with the surface of the organ.

8. A method comprising:
 engaging a seal member having a chamber with an organ;
 coupling a source of vacuum pressure to the seal member, the source of vacuum pressure being in fluid communication with the chamber through a valve;
 applying vacuum pressure to the chamber such that a portion of the seal member deforms to substantially seal the chamber against leakage; and
 closing the valve to maintain the seal.

9. The method of claim 8 further comprising uncoupling the source of vacuum pressure to the seal member after closing the valve.

10. The method of claim 8 further comprising opening the valve to break the seal.

11. The method of claim 10 further comprising applying positive pressure to the chamber to disengage the seal member from the organ.

12. An organ manipulation device comprising:
 a seal member having a wall defining a chamber and a skirt-like member that extends outward from the wall for contact with a surface of an organ, wherein the skirt-like member is substantially compliant and tacky, thereby promoting adhesion with the surface of the organ;
 a fluid tube in fluid communication with the interior of the chamber; and
 a valve to regulate fluid flow through the fluid tube.

13. The device of claim 1, further comprising a swivel connection that couples the seal member to the fluid tube.

14. The device of claim 13, wherein the swivel connection is formed integrally with the wall.

15. The device of claim 1, wherein the seal member comprises a flexible stem extending away from the skirt-like member, the flexible stem coupling the seal member to the fluid tube.

16. The device of claim 15, wherein the flexible stem is formed integrally with the wall.

17. The device of claim 1, further comprising a connector that couples the seal member to the fluid tube, wherein the seal member defines a notch-out area that accommodates the fluid tube when the fluid tube is positioned at an angle relative to the seal member.

18. The method of claim 8, wherein applying vacuum pressure to the chamber comprises applying vacuum pressure to the chamber via a vacuum tube coupled to the chamber, the method further comprising holding the vacuum tube while accommodating the motions of the heart as the heart beats.

19. The method of claim 18, wherein accommodating the motions of the heart as the heart beats comprises accommodating twisting motions and translational motions.

20. The method of claim 8, wherein applying vacuum pressure to the chamber comprises applying vacuum pressure to the chamber via a vacuum tube coupled to the chamber, the method further comprising securing the vacuum tube to an immobile object while accommodating the motions of the heart as the heart beats.

21. The method of claim 8, further comprising:
   coupling a vacuum tube to the seal member; and
   positioning the vacuum tube an angle relative to the seal member.

22. The method of claim 21, further comprising coupling a vacuum tube to the seal member with a swivel connection.

23. The device of claim 12, further comprising a swivel connection that couples the seal member to the fluid tube.

24. The device of claim 23, wherein the swivel connection is formed integrally with the wall.

25. The device of claim 12, wherein the seal member comprises a flexible stem extending away from the skirt-like member, the flexible stem coupling the seal member to the fluid tube.

26. The device of claim 25, wherein the flexible stem is formed integrally with the wall.

27. The device of claim 12, further comprising a connector that couples the seal member to the fluid tube, wherein the seal member defines a notch-out area that accommodates the fluid tube when the fluid tube is positioned at an angle relative to the seal member.

* * * * *